(12) United States Patent
Mehrabi et al.

(10) Patent No.: US 8,623,986 B2
(45) Date of Patent: Jan. 7, 2014

(54) GELS

(75) Inventors: Mansour Mehrabi, Victoria (AU);
Sriram Venkataramani, Victoria (AU);
Mark Bown, Notting Hill (AU); Ajay Padsalgikar, Wheelers Hill (AU)

(73) Assignee: Aertech International plc (GB)

( * ) Notice: Subject to any disclaimer, the term of this patent is extended or adjusted under 35 U.S.C. 154(b) by 1010 days.

(21) Appl. No.: 12/226,508

(22) PCT Filed: Apr. 19, 2007

(86) PCT No.: PCT/AU2007/000511
§ 371 (c)(1),
(2), (4) Date: Jun. 22, 2009

(87) PCT Pub. No.: WO2007/121513
PCT Pub. Date: Nov. 1, 2007

(65) Prior Publication Data
US 2010/0029802 A1   Feb. 4, 2010

Related U.S. Application Data

(60) Provisional application No. 60/802,080, filed on May 18, 2006.

(30) Foreign Application Priority Data

Apr. 20, 2006   (AU) .............................. 2006902072

(51) Int. Cl.
*C08G 77/14* (2006.01)
*C08G 77/26* (2006.01)
*A61F 2/02* (2006.01)

(52) U.S. Cl.
USPC .................. 528/28; 528/24; 528/29; 528/38; 523/113

(58) Field of Classification Search
None
See application file for complete search history.

(56) References Cited

U.S. PATENT DOCUMENTS

| | | | |
|---|---|---|---|
| 3,398,172 A | | 8/1968 | Klaus et al. |
| 4,585,534 A | * | 4/1986 | Pasternack et al. ............. 522/31 |
| 4,614,760 A | * | 9/1986 | Homan et al. ................ 524/860 |
| 5,187,251 A | * | 2/1993 | Jachmann et al. .............. 528/15 |
| 5,336,797 A | | 8/1994 | McGee et al. |
| 5,403,912 A | | 4/1995 | Gunatillake |
| 5,451,617 A | | 9/1995 | Lai et al. |
| 5,863,627 A | | 1/1999 | Szycher et al. |
| 6,313,254 B1 | | 11/2001 | Meijs et al. |
| 6,627,724 B2 | | 9/2003 | Meijs et al. |
| 6,803,399 B2 | * | 10/2004 | Ferritto et al. ................. 524/267 |
| 8,207,245 B2 | | 6/2012 | Padsalgikar et al. |
| 2003/0018156 A1 | | 1/2003 | Meijs et al. |
| 2003/0125498 A1 | | 7/2003 | McCabe et al. |
| 2004/0054080 A1 | | 3/2004 | Benz et al. |
| 2006/0106458 A1 | * | 5/2006 | Jason et al. .................. 623/6.11 |
| 2006/0223964 A1 | | 10/2006 | Lai et al. |
| 2008/0293844 A1 | | 11/2008 | Padsalgikar et al. |
| 2010/0029802 A1 | | 2/2010 | Mehrabi et al. |

FOREIGN PATENT DOCUMENTS

| | | |
|---|---|---|
| AU | 2007242052 | 11/2007 |
| AU | 2005289374 | 10/2011 |
| EP | 1081272 A1 | 3/2001 |
| EP | 1251146 A1 | 10/2002 |
| EP | 1081272 B1 | 10/2004 |
| EP | 1251146 B1 | 9/2006 |
| EP | 2007826 A1 | 12/2008 |
| JP | 62-224051 | 10/1987 |
| JP | 62224051 A | 10/1987 |
| JP | 2001500912 A | 1/2001 |
| JP | 2001526727 A | 12/2001 |
| JP | 2002509958 A | 4/2002 |
| JP | 2002543231 A | 12/2002 |
| JP | 2003505562 A | 2/2003 |
| JP | 2006510750 A | 3/2006 |
| WO | WO-9305098 A1 | 3/1993 |
| WO | WO-9813405 A1 | 4/1998 |
| WO | WO-9854242 A1 | 12/1998 |
| WO | WO-9950327 A1 | 10/1999 |
| WO | WO-0064971 A1 | 11/2000 |
| WO | WO-0107499 A1 | 2/2001 |
| WO | WO 2004/011529   * | 2/2004 |
| WO | WO-2004/011529 A1 | 2/2004 |
| WO | WO-2004034547 A1 | 4/2004 |
| WO | WO-2004/052963 A1 | 6/2004 |
| WO | WO-2004062531 A1 | 7/2004 |
| WO | WO-2005005517 A2 | 1/2005 |

(Continued)

OTHER PUBLICATIONS

"International Application Serial No. PCT/AU2007/000511, International Preliminary Report on Patentability mailed Aug. 22, 2008", 9 pgs.
"International Application Serial No. PCT/AU2007/000511, International Search Report mailed Jun. 28, 2007", 3 pgs.
"International Application Serial No. PCT/AU2007/000511, Response filed Jan. 24, 2008 to Written Opinion mailed Jun. 20, 2007", 6 pgs.
"International Application Serial No. PCT/AU2007/000511, Response filed Apr. 8, 2008 to Written Opinion mailed Jun. 20, 2007", 3 pgs.

(Continued)

*Primary Examiner* — Marc Zimmer
(74) *Attorney, Agent, or Firm* — Schwegman Lundberg & Woessner, P.A.

(57) ABSTRACT

The present invention relates to biostable gel comprising:
(a) at least one silicon-containing polyol, polyamine, polyepoxy or polyisocyanate having 1 or more functional groups and a molecular weight of at least 20,000 which is cured in the presence of:
(b) at least one diol, diamine or diisocyanate having a molecular weight of less than 10,000; and/or
(c) an initiator,
processes for their preparation and their use in the manufacture and repair of biomaterials and medical devices, articles or implants, in particular the manufacture of a soft tissue implant such as breast implants and the repair of orthopaedic joints such as spinal discs.

32 Claims, No Drawings

(56) References Cited

FOREIGN PATENT DOCUMENTS

| WO | WO 2006/034547 | * | 4/2006 |
|---|---|---|---|
| WO | WO-2006/034547 A1 | | 4/2006 |
| WO | WO-2006107899 A1 | | 10/2006 |

OTHER PUBLICATIONS

"International Application Serial No. PCT/AU2007/000511, Second Written Opinion mailed May 30, 2008", 4 pgs.
"International Application Serial No. PCT/AU2007/000511, Written Opinion mailed Jun. 20, 2007", 6 pgs.
"U.S. Appl. No. 11/663,870, Final Office Action mailed Dec. 27, 2010", 8 pgs.
"U.S. Appl. No. 11/663,870, Non Final Office Action mailed Sep. 16, 2011", 6 pgs.
"U.S. Appl. No. 11/663,870, Non-Final Office Action mailed Apr. 2, 2010", 9 pgs.
"U.S. Appl. No. 11/663,870, Notice of Allowance mailed Feb. 28, 2012", 7 pgs.
"U.S. Appl. No. 11/663,870, Preliminary Amendment filed Mar. 27, 2007", 14 pgs.
"U.S. Appl. No. 11/663,870, Response filed Feb. 14, 2012 to Non Final Office Action mailed Sep. 16, 2011", 9 pgs.
"U.S. Appl. No. 11/663,870, Response filed Jun. 24, 2011 to Final Office Action mailed Dec. 27, 2010", 10 pgs.
"U.S. Appl. No. 11/663,870, Response filed Oct. 4, 2010 to Non Final Office Action mailed Apr. 2, 2010", 16 pgs.
"U.S. Appl. No. 11/663,870, Restriction Requirement mailed May 27, 2010", 7 pgs.
"U.S. Appl. No. 11/663,870, Response filed Nov. 3, 2009 to Restriction Requirement mailed May 27, 2009", 13 pgs.
"Australian Application Serial No. 2004905628, Australian Search Report mailed Jan. 19, 2005", 2 pgs.
"Australian Application Serial No. 2005289374, Office Action mailed Apr. 28, 2011", 2 pgs.
"Australian Application Serial No. 2005289374, Office Action mailed May 26, 2010", 3 pgs.
"Australian Application Serial No. 2005289374, Response filed Apr. 15, 2011 to Office Action mailed May 26, 2010", 5 pgs.
"Australian Application Serial No. 2005289374, Response filed Jun. 15, 2011 to Office Action mailed Apr. 28, 2011", 2 pgs.
"Australian Application Serial No. 2007242052, Office Action mailed Oct. 17, 2011", 2 pgs.
"Australian Application Serial No. 2007242052, Response filed Aug. 16, 2012 to Office Action mailed Oct. 17, 2011", 31 pgs.
"Chinese Application Serial No. 200580032323.8, Amendment filed Dec. 3, 2010", with English translation of claims, 15 pgs.
"Chinese Application Serial No. 200580032323.8, Notice of Allowance mailed Feb. 12, 2011", with English translation, 5 pgs.
"Chinese Application Serial No. 200580032323.8, Office Action mailed Feb. 20, 2009", with English translation of claims, 27 pgs.
"Chinese Application Serial No. 200580032323.8, Office Action mailed Nov. 20, 2009", with English translation of claims, 12 pgs.
"Chinese Application Serial No. 200580032323.8, Office Action mailed Dec. 1, 2010", In English only, 10 pgs.
"Chinese Application Serial No. 200580032323.8, Response filed Apr. 2, 2010 to Office Action mailed Nov. 20, 2009", w/ English Translation, 17 pgs.
"Chinese Application Serial No. 200580032323.8, Response filed Sep. 7, 2009 to Office Action mailed Feb. 20, 2009", w/ English Translation, 19 pgs.
"European Application Serial No. 05791328.7, Office Action mailed Feb. 11, 2011", 4 pgs.

"European Application Serial No. 05791328.7, Office Action mailed May 15, 2007", 2 pgs.
"European Application Serial No. 05791328.7, Office Action mailed Jun. 22, 2010", 1 pgs.
"European Application Serial No. 05791328.7, Response filed Aug. 18, 2011 to Office Action mailed Feb. 11, 2011", 12 pgs.
"European Application Serial No. 05791328.7, Response filed Dec. 29, 2010 to Office Action mailed Jun. 22, 2010", 22 pgs.
"European Application Serial No. 05791328.7, Supplementary European Search Report mailed Mar. 4, 2010", 5 pgs.
"European Application Serial No. 07718758.1, European Search Report mailed Jun. 2, 2009", 10 pgs.
"European Application Serial No. 07718758.1, Office Action mailed Jul. 1, 2010", 6 pgs.
"European Application Serial No. 07718758.1, Office Action mailed Oct. 14, 2009", 1 pgs.
"European Application Serial No. 07718758.1, Office Action mailed Nov. 10, 2011", 3 pgs.
"European Application Serial No. 07718758.1, Office Action mailed Nov. 27, 2008", 2 pgs.
"European Application Serial No. 07718758.1, Response filed Jan. 2, 2009 to Office Action mailed Nov. 27, 2008", 11 pgs.
"European Application Serial No. 07718758.1, Response filed Mar. 15, 2012 to Office Action mailed Nov. 10, 2011", 44 pgs.
"European Application Serial No. 07718758.1, Response filed Apr. 23, 2010 to EP Office Action mailed Oct. 14, 2009", 12 pgs.
"European Application Serial No. 07718758.1, Response filed Dec. 31, 2010 to EP Office Action mailed Jul. 1, 2010", 9 pgs.
"India Application Serial No. 1026/KOLNP/2007, First Examiner Report mailed Dec. 10, 2010", 2 pgs.
"Indian Application Serial No. 1026/KOLNP/2007, Response filed May 2, 2012 to Office Action mailed Apr. 2, 2012", 14 pgs.
"Indian Application Serial No. 1026/KOLNP/2007, Subsequent Examiners Report Mailed Apr. 2, 2012", 4 Pgs.
"International Application Serial No. PCT/AU2005/001491, International Search Report mailed on Jan. 3, 2006", 3 pg.
"International Application Serial No. PCT/AU2005/001491, International Preliminary Report on Patentability mailed Dec. 11, 2006", 4 pgs.
"International Application Serial No. PCT/AU2005/001491, Written Opinion mailed Jan. 3, 2006", 4 pgs.
"International Application Serial No. PCT/AU2007/000511, International Preliminary Report on Patentability mailed Aug. 18, 2008", 8 pgs.
"International Application Serial No. PCT/AU2007/000511, International Search Report mailed Jun. 28, 2007", 8 pgs.
"International Application Serial No. PCT/AU2007/000511, Written Opinion mailed Jun. 20, 2007", 4 pgs.
"Japanese Application Serial No. 2007-533824, First Office Action mailed Oct. 13, 2011", with English translation of claims, 7 pgs.
"Japanese Application Serial No. 2007-533824, Office Action Response Filed Mar. 14, 2012", With English Claims, 14 Pgs.
"Japanese Application Serial No. 2009-505683, Office Action mailed Sep. 4, 2012", With English Translation, 5 pgs.
Van Bommel, M. J, "The influence of the addition of alkyl-substituted ethoxysilane on the hydrolysiscondensation process of TEOS", Journal of Non-Crystallines Solids 128, (1991), 231-242.
"European Application Serial No. 07718758.1, Office Action mailed Apr. 10, 2013", 87 pgs.
"Japanese Application Serial No. 2007-533824, Office Action mailed Oct. 16, 2012", with English translation of claims, 6 pgs.
"Japanese Application Serial No. 2009-505683, Response filed Mar. 7, 2013 to Office Action mailed Sep. 4, 2012", with English translation of claims, 29 pgs.

* cited by examiner

GELS

RELATED APPLICATIONS

This application is a nationalization under 35 U.S.C. 371 of PCT/AU2007/000511, filed Apr. 19, 2007 and published as WO 2007/121513 A1, on Nov. 1, 2007, which claimed priority under 35 U.S.C. 119 to Australian Application No. 2006902072, filed Apr. 20, 2006; and which claimed priority under 35 U.S.C. 119(e) to U.S. Provisional Patent Application Ser. No. 60/802,080, filed May 18, 2006; which applications and publication are incorporated herein by reference and made a part hereof.

FIELD

The present invention relates to silicon-containing biostable gels and processes for their preparation. The gels possess properties which make them useful in the manufacture and repair of biomaterials and medical devices, articles or implants, in particular the manufacture of soft tissue implants such as breast implants and the repair of orthopaedic joints such as spinal discs.

BACKGROUND

Polymer gels are semi-solid systems that respond in a liquid like fashion under certain circumstances but their molecules do not have motion that is independent of each other, hence they behave like solids in other circumstances.

Gels can be synthesised as physical gels where a cross-linked network is swelled by a non reactive liquid. Without the presence of this swelling medium the cross-linked network would be a solid. Silicone gels currently used in breast implants are physical gels where a cross-linked polydimethylsiloxane (PDMS) system is swollen by a non reactive, low molecular weight PDMS. These gels are inherently prone to leakage of the low molecular weight liquid PDMS and contain heavy metal catalysts such as platinum and tin which can leach out of the implant in an in-vivo situation.

Hydrogels are other examples of physical gels, where hydrophilic groups in the cross-linked network can attract water molecules and are swollen by them. In a physical gel the parts by weight of the swelling medium can be as high as 90%. This swelling medium can be extracted out of the gel by most solvents and biological fluids.

There is a need for a gel that mimics the behaviour of a PDMS-based physical gel, but is chemically formulated so as to avoid the complications of a physical gel.

SUMMARY

International Patent Publication No. WO 2006/034547 describes silicon-containing biostable gels. We have now found that increasing the molecular weight of the silicon-containing component of the gels specifically disclosed in WO 2006/034547 allows curing to occur at room temperature. The use of higher molecular weight components also increases the stoichiometry of curing which assists in reducing the amount of solvent extractables which are free to migrate from the gel.

According to the present invention there is provided a biostable gel comprising:

(a) at least one silicon-containing polyol, polyamine, polyepoxy or polyisocyanate having 1 or more functional groups and a molecular weight of at least 20,000 which is cured in the presence of:

(b) at least one diol, diamine or diisocyanate having a molecular weight of less than 10,000; and/or (c) an initiator.

The amount of polyol, polyamine, polyepoxy or polyisocyanate (a) present in the gel is preferably 80 to 100% and the amount of diol, diamine or diisocyanate (b) is preferably 0 to 20% based on the total weight of the gel.

The molecular weight of diol, diamine or diisocyanate is preferably 500 to 10000, more preferably 2000 to 6000.

The gel preferably has an average functionality of 1 to 5, more preferably 2.05 to 3.5, most preferably 2.1 to 3.25.

The present invention also provides a process for preparing the biostable gel defined above which comprises the steps of:

(i) mixing components (a) and (b) or (c) as defined above.

In another embodiment, the process for preparing the biostable gel defined above comprises the steps of:

(i) preparing a prepolymer having terminally reactive polyisocyanate groups from component (b) defined above; and (ii) mixing the prepolymer of step (i) with component (a) as defined above.

Some of the silicon-containing polyols, polyamines, polyepoxys or polyisocyanates (a) defined above are novel and form part of the invention.

Further according to the present invention there is provided a silicon-containing polyol, polyamine, polyepoxy or polyisocyanate of formula (I) or (II):

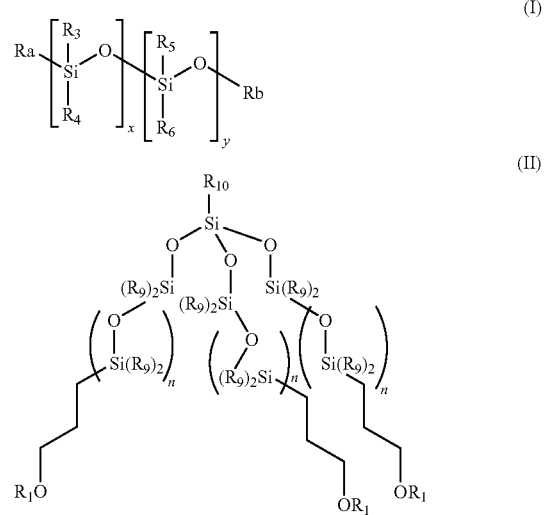

in which $R_a$ and $R_b$ are both absent or independently selected from $C_{1-6}$alkyl, OH, $C_{1-6}$alkoxy, $(CH_2)_3OR_1$, and $Si(R_7)(R_8)(CH_2)_3OR_2$;

$R_1$ and $R_2$ are independently selected from $C_{1-6}$ alkylene optionally substituted with OH, NCO, expoxy or NR'R" in which R' and R" are independently selected from H, $CO_2H$ and $C_{1-6}$ alkyl;

$R_3$ to $R_8$ are independently selected from vinyl, $C_{1-6}$ alkyl and $C_{1-6}$ alkylene which may be optionally interrupted by O and optionally substituted with OH, NCO, epoxy, $C_{1-6}$alkyl acrylate or NR'R" in which R' and R" are as defined above;

$R_9$ is $C_{1-4}$ alkyl;
$R_{10}$ is optionally substituted $C_{1-4}$ alkyl or

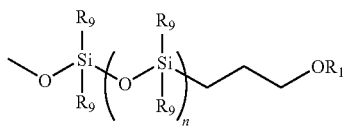

in which $R_1$ and $R_9$ are as defined above;
x is 100 to 1000, preferably 300 to 600;
y is 0 to 200, preferably 0 to 10; and
n is 30 to 500, preferably 50 to 200.

The present invention further provides a process for the preparation of the silicon-containing polyol, polyamine, polyepoxy or polyisocyanate of formula (I) or (II) defined above which comprises the steps of:
(i) reacting a compound of formula (A) or (B)

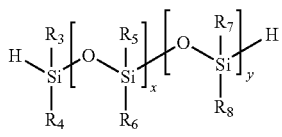

(A)

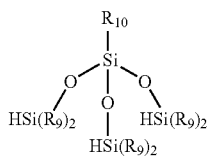

(B)

in which $R_3$ to $R_{10}$ and x and y are as defined above with a compound of formula (C)

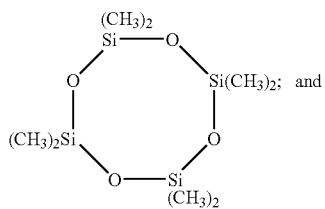

(C)

(ii) subjecting the product of step (i) to hydrosilation.

The gels of the present invention possess visco-elastic properties and have a natural tissue feel to suit, for example, soft tissue implant gel applications such as breast implants. These gels also have a low level of extractables preferably less than 15%, more preferably less than 10%, most preferably less than 5% based on the total weight of the gel.

In a particularly preferred embodiment suitable for breast implant applications, the gel is a reaction product of:
(a) the silicon-containing polyol, polyamine, polyepoxy or polyisocyanate of formula (I) or (II) defined above; and
(b) $C_{1-6}$ alkane diol or diamine, polysiloxane diol or diamine such as PDMS and/or a diisocyanate such as MDI.

Thus, the present invention also provides a biomaterial, device, article or implant which is wholly or partly composed of the gels defined above.

The present invention further provides a filler material for a medical implant such as a breast implant which comprises the gel defined above.

DETAILED DESCRIPTION

The biostable silicon-containing gel of the present invention is a chemical gel. When a cross-linked network is formulated such that the reactive groups are in a perfect balance then, during the course of the reaction, the network begins to vitrify and ends up being a hard solid. If the reaction is not allowed to go to completion by creating an imbalance in the reactive groups, then an off-stoichiometric system occurs which is capable of gelation. Thus, one reactive group is in excess and remains incompletely reacted. This excess amount acts similar to the non-reactive swelling medium in physical gels. However, usually lower amounts of unreacted material, in comparison to the swelling agents, can be formulated to achieve a similar effect to a physical gel and that, in turn, implies lower extractable species. The level of extractables in the gel of the present invention is preferably less than 15%, more preferably less than 10%, most preferably less than 5% based on the total weight of the gel.

The term "extractables" refers to the unreacted portion of the gel which is generally fluid and free to migrate out of the gel at body temperature of 38° C. and more specifically, refers to the unreacted fluid portion of a gel which is extracted by organic solvents at temperatures in the range from 20° C. to 40° C.

The term "biostable" refers to the stability of the polymer when in contact with cells and/or bodily fluids of living animals or humans.

The term "average functionality" of a polymerisation system refers to the average number of functional groups per monomer for all types of monomer molecules and is defined by the following formula:

$$f_{avg} = \frac{\sum_i n_i f_i}{\sum_i n_i}$$

in which
$n_i$ is number of molecules of monomer i with functionality groups $f_i$.

Preferably, the average functionality of the gel is 2 to 5, more preferably 2.05 to 3.5, most preferably 2.1 to 3.25.

The components (a) and (b) are preferably mixed so that the NCO/OH or $NH_2$ ratio is less than 1, more preferably from 0.4 to 0.7 so as to provide the appropriate rheological response.

It will be understood that the molecular weight values referred to herein are "number average molecular weights".

Silicon-Containing Polyol, Polyamine, Polyepoxy or Polyisocyanate

The silicon-containing polyol, polyamine, polyepoxy or polyisocyanate (a) can have 1 or more functional groups provided that the average functionality of the gel is preferably 1 to 5. Component (a) is preferably a long chain macromer.

The functional groups of component (a) are preferably independently selected from OH, NCO, epoxy and NR'R" in which R' and R" are independently selected from H, $CO_2H$ and $C_{1-6}$ alkyl, preferably H and $C_{1-4}$ alkyl or are groups capable of activation by free radical initiation such as groups containing double or triple bonds, for example, vinyl or $C_{1-6}$alkyl acrylates.

Suitable silicon-containing polyols, polyepoxys polyamines or polyisocyanates (a) include compounds of the formula (I) or (II) defined above such as T-triols, T-vinylsiloxanes, T-epoxysiloxanes and T-triisocyanates.

Representative examples of compounds of the formula (I) are as follows:
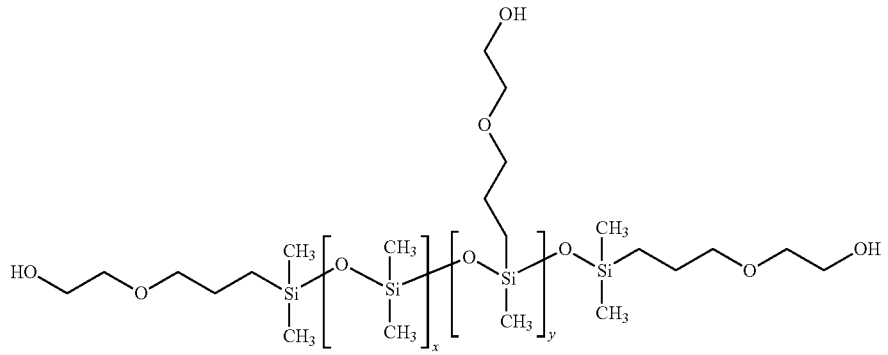
(Ia)
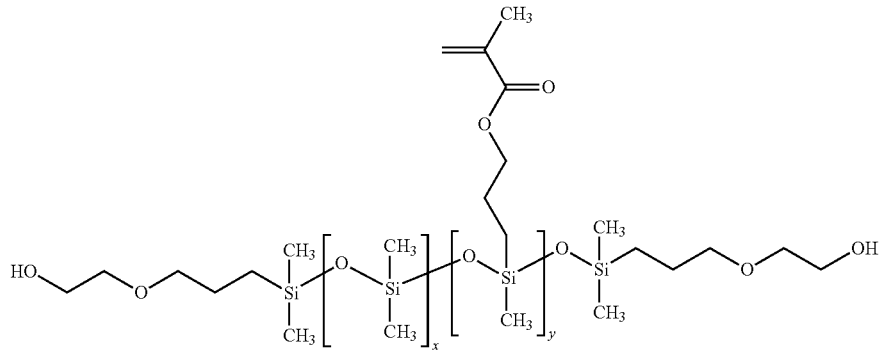
(Ib)
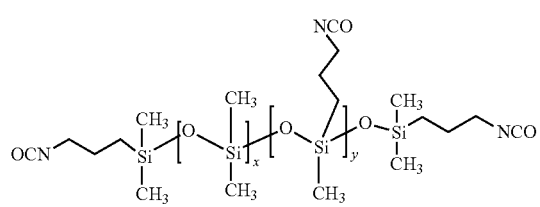
(Ic)
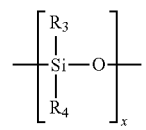
(Id)
$R_3$ = Vinyl;
$R_4$ = $C_{1-6}$ alkyl;
x = 100 to 1000
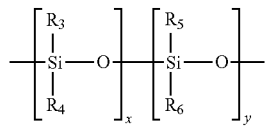
(Ie)
$R_3$ = Vinyl; $R_4$, $R_5$ and $R_6$ = $C_{1-6}$ alkyl; x = 100 to 1000 and y = 4 to 200
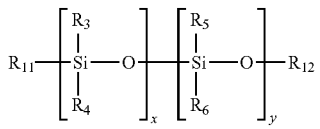
(If)
$R_3$ = Vinyl; $R_4$, $R_5$ and $R_6$ = $C_{1-6}$ alkyl; $R_{11}$ and $R_{12}$ = $C_{1-6}$ alkyl, hydroxyl, methoxy and/or ethoxy; x = 100 to 1000 and y = 4 to 200
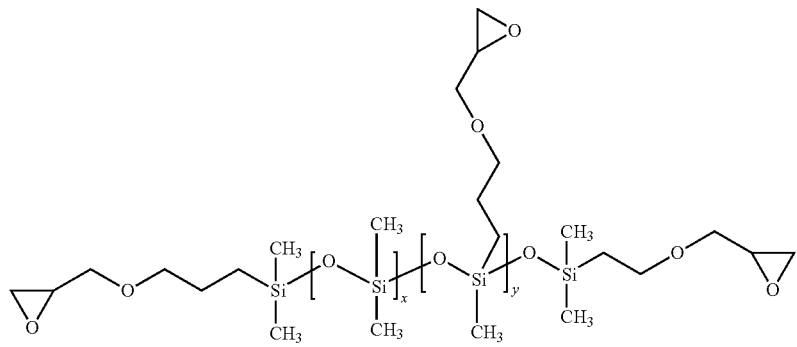
(Ig)

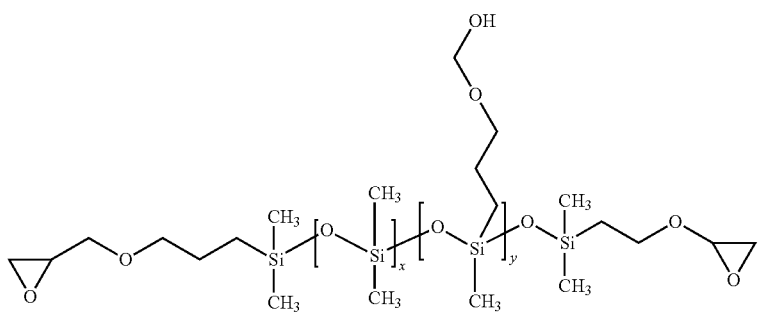

(Ih)

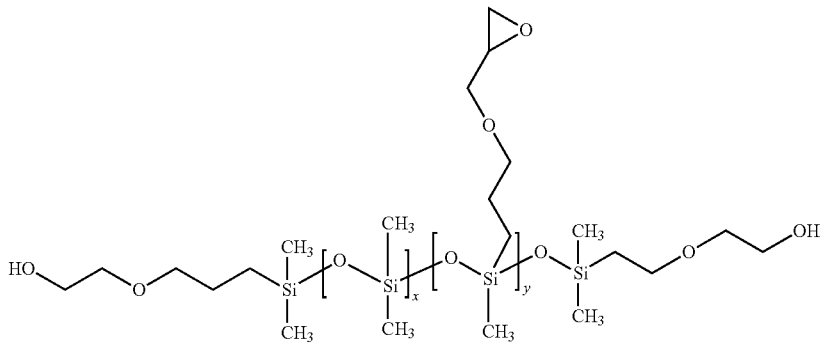

(Ii)

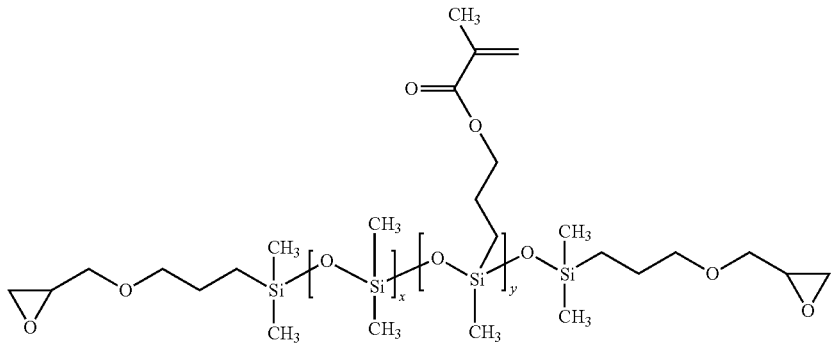

(Ij)

A representative example of a compound of the formula (II) is as follows:

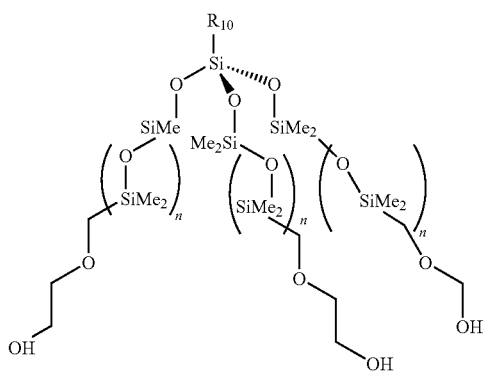

(IIa)

The molecular weight of component (a) is at least 20,000, preferably 30,000 to 200,000, more preferably 40,000 to 80,000.

Diol or Diamine

The diol or diamine may be a polyether, polycarbonate, polyalkylene or $C_{1-6}$ alkane. The diol or diamine may also contain silicon such as a polysiloxane diol or diamine or a silicon-based polycarbonate.

Suitable polyether diols and diamines include those represented by the formula (III)

$$A-[(CH_2)_m—O]_n-A' \qquad (III)$$

in which

A and A' are OH or NHR wherein R is H or optionally substituted $C_{1-6}$ alkyl, more preferably optionally substituted $C_{1-4}$ alkyl;

m is an integer of 4 or more, preferably 4 to 18; and n is an integer of 2 to 50.

Polyether macrodiols of formula (III) wherein m is 4 to 10 such as polytetramethylene oxide (PTMO), polyhexamethylene oxide (PHMO), polyheptamethylene oxide, polyoctamethylene oxide (POMO) and polydecamethylene oxide (PDMO) are preferred.

The preferred molecular weight range of the polyether is 200 to 5000, more preferably 200 to 2000.

Suitable polycarbonate diols include poly(alkylene carbonates) such as poly(hexamethylene carbonate) and poly (decamethylene carbonate); polycarbonates prepared by reacting alkylene carbonate with alkanediols for example 1,4-butanediol, 1,10-decanediol (DD), 1,6-hexanediol (HD) and/or 2,2-diethyl 1,3-propanediol (DEPD); and silicon based polycarbonates prepared by reacting alkylene carbonate with 1,3-bis(4-hydroxybutyl)-1,1,3,3-tetramethyldisiloxane (BHTD) and/or alkanediols.

It will be appreciated when both the polyether and polycarbonate macrodiols are present, they may be in the form of a mixture or a copolymer. An example of a suitable copolymer is a copoly(ether carbonate) macrodiol represented by the formula (IV)

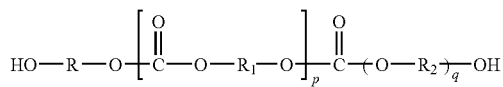

(IV)

in which $R_1$ and $R_2$ are the same or different and selected from an optionally substituted $C_{1-6}$ alkylene, $C_{2-6}$ alkenylene, $C_{2-6}$ alkynylene, arylene or a heterocyclic divalent radical; and p and q are integers of 1 to 20.

Although the compound of formula (IV) above indicates blocks of carbonate and ether groups, it will be understood that they also could be distributed randomly in the main structure.

Examples of $C_{1-6}$ alkane diols or diamines include methane diol, butane diol or hexane diol.

A preferred polysiloxane is PDMS which is a compound of formula (V) in which A and A' are hydroxyl, $R_{11}$ to $R_{14}$ are methyl and $R_{15}$ and $R_{16}$ are as defined above. Preferably $R_{15}$ and $R_{16}$ are the same or different and selected from propylene, butylene, pentylene, hexylene, ethoxypropyl ($-CH_2CH_2OCH_2CH_2CH_2-$), propoxypropyl and butoxypropyl.

Other silicon-containing diols of the formula (V) are 1,3-bis(4-hydroxybutyl)tetramethyl disiloxane (BHTD) (compound of formula (V) in which A and A' are OH, $R_{11}$, $R_{12}$, $R_{13}$ and $R_{14}$ are methyl, $R_{15}$ and $R_{16}$ are butyl and $R_{17}$ is O), 1,4-bis(3-hydroxypropyl)tetramethyl disilylethylene (compound of formula (V) in which A and A' are OH, $R_{11}$, $R_{12}$, $R_{13}$ and $R_{14}$ are methyl, $R_{15}$ and $R_{16}$ are propyl and $R_{17}$ is ethylene) and 1-4-bis(3-hydroxypropyl)tetramethyl disiloxane, more preferably BHTD.

The polysiloxanes may be obtained as commercially available products such as X-22-160AS from Shin Etsu in Japan or prepared according to known procedures. The preferred molecular weight range of the polysiloxane macrodiol is 200 to 6000, more preferably from 200 to 5000.

Other preferred polysiloxanes are polysiloxane macrodiamines which are polymers of the formula (V) wherein A is $NH_2$, such as, for example, amino-terminated PDMS.

Suitable silicon-containing polycarbonates include those described in International Patent Publication No. WO 98/54242, the entire content of which is incorporated herein by reference.

A preferred silicon-containing polycarbonate has the formula (VI):

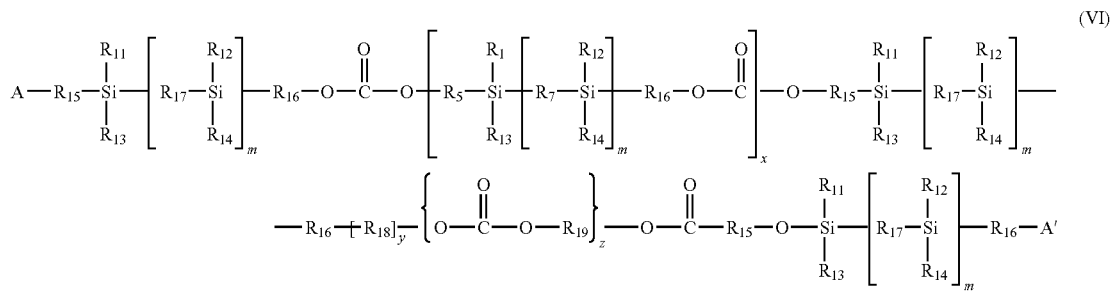

(VI)

Suitable polysiloxane diols or diamines are represented by the formula (V):

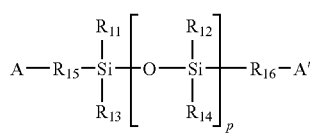

(V)

in which

A and A' are OH or NHR wherein R is H or optionally substituted $C_{1-6}$ alkyl, more preferably optionally substituted $C_{1-4}$ alkyl;

$R_{11}$, $R_{12}$, $R_{13}$ and $R_{14}$ are independently selected from hydrogen or optionally substituted $C_{1-6}$ alkyl;

$R_{15}$ and $R_{16}$ are the same or different and selected from optionally substituted $C_{1-6}$ alkylene, $C_{2-6}$ alkenylene, $C_{2-6}$ alkynylene, arylene or a heterocyclic divalent radical; and p is an integer of 1 or greater.

in which $R_{11}$, $R_{12}$, $R_{13}$, $R_{14}$ and $R_{15}$ are as defined in formula (V) above;

$R_{16}$ is an optionally substituted $C_{1-6}$ alkylene, $C_{2-6}$ alkenylene, $C_{2-6}$ alkynylene, arylene or a heterocyclic divalent radical;

$R_{17}$ is a divalent linking group, preferably O, S or $NR_{18}$;

$R_{18}$ and $R_{19}$ are same or different and selected from hydrogen or optionally substituted $C_{1-6}$ alkyl;

A and A' are as defined in formula (V) above;

m, y and z are integers of 0 or more; and x is an integer of 0 or more.

Preferably z is an integer of 0 to 50 and x is an integer of 1 to 50. Suitable values for m include 0 to 20, more preferably 0 to 10. Preferred values for y are 0 to 10, more preferably 0 to 2.

A preferred silicon-containing polycarbonate is a compound of the formula (VI) in which A and A' are hydroxyl.

Particularly preferred silicon-containing polycarbonate diols are compounds of the formula (VI) in which A and A' are hydroxyl, $R_{11}$, $R_{12}$, $R_{13}$ and $R_{14}$ are methyl, $R_{18}$ is ethyl, $R_{19}$ is hexyl, $R_{15}$ and $R_{16}$ are propyl or $R_{14}$ butyl and $R_{17}$ is 0 or —$CH_2$—$CH_2$—, more preferably $R_5$ and $R_{16}$ are propyl when $R_{17}$ is 0 and $R_{15}$ and $R_{16}$ are butyl when $R_{17}$ is —$CH_2$—$CH_2$—. The preferred molecular weight range of the silicon-based polycarbonate macrodiol is from 400 to 5000, more preferably from 400 to 2000.

Diisocyanate

The diisocyanate may be an aliphatic or aromatic diisocyanate such as 4,4'-diphenylmethane diisocyanate (MDI), methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanatonaphthalene (NDI), para-tetramethylxylenediisocyanate (p-TMXDI), meta-tetramethylxylene diisocyanate (m-TMXDI), 2,4-toluene diisocyanate (2,4-TDI) isomers or mixtures thereof or isophorone diisocyanate (IPDI). Aromatic diisocyanates such as MDI are preferred.

Initiator

The term "initiator" refers to at least one molecule which when activated by an energy source, will result in free radical polymerisation of polymers in a curing step. The energy source initiating the polymerisation may be thermal, photolytic or based on a redox system of components with the result that free radical polymerization occurs to cure the prepolymer composition.

The selection of the initiator for the purpose of triggering free radical curing is dependent on the method of initiation selected. Initiation may be thermal, photolytic or based on a redox system of components and is preferably by an external source. For example, camphorquinone, phosphine oxide based initiators such as (2,4,6-trimethyl benzoyl) diphenyl phosphine oxide are suitable and redox initiators such as ammonium persulfate and sodium metabisulfite, gamma radiation or ultrasound are also suitable. For in-vivo applications photolytic initiators or redox based systems are preferred. More preferable is a system that cures the polymer using a wave length that is either in the UV or visible region of electromagnetic radiation. Of the two, visible light initiation is more desirable in biomedical applications. In one embodiment of the invention, visible light source having a maximum wave length of 450±30 nm is used. Examples of photoinitiators include but are not limited to 2,2-dimethoxy-2-phenylacetophenone (Irgacure 651), hydroxyalkyl phenones (1-hydroxycyclohexyl phenyl ketone (Irgacure 184), 2-methyl-1-[4-(methylthio)phenyl]-2-(4-morpholinyl)-1-propanone (Irgacure 907), 2-hydroxy-1-[4-(hydroxyethoxy) phenyl]-2-methyl-1-propanone (Darocur 2959), Darocur 4265, Darocur TPO, Darocur 1173, Irgacure 500, 784, 907, 2959, 819, 2020, 2022, 1000, 369, 651, 1300, 819/819W, 2005 and 2010W, Dragacure 1173, polysilanes, Esacure KP150 (hydroxyalkylphenylketone), camphorquinone, Rosebengal, ethyl-4-N,N-dimethylamino-benzoate (4EDMAB)/triethanolamine, α alkoxydeoxybenzoins, α,α-dialkoxy-acetophenone (DEAP), (1-hydroxy-cyclohexyl-phenylketone), dibenzoyl disulphide, S-phenyl thiobenzoates, acylphosphine oxide, dibenzoylmethanes, O-acyl α-oximinoketones, phenylazo-4-diphenyl sulphone, benzophenones, flourenones, xanthones, thioxanthones, benzils, ketals (2,2-dimethoxy-2-phenylacetophenone DMP), α-ketocoumarines, anthraquinone, ethyl eosin and terephthalophenones. Examples of free radical initiators include benzoyl peroxide and cumyl peroxide.

The amount of initiator (c) is preferably 0.125% to 5%, more preferably 0.25% to 2% based on the total weight of the gel.

CHEMICAL DEFINITIONS

The term "$C_{1-6}$alkylene" is a divalent radical equivalent of the term "$C_{1-6}$ alkyl". The two bonds connecting the alkylene to the adjacent groups may come from the same carbon atom or difference carbon atoms in the divalent radical.

The term "$C_{1-6}$alkyl" denotes straight chain, branched or mono- or poly-cyclic alkyl having 1 to 6 carbon atoms, preferably $C_{1-4}$ alkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, pentyl, neopentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl and the like. Examples of cyclic alkyl include cyclopropyl, cyclobutyl, cyclopentyl, cyclohexyl and the like.

The term "$C_{2-6}$alkenyl" denotes groups formed from straight chain, branched or mono- or poly-cyclic hydrocarbon groups having at least one double bond. The alkenyl group may have E or Z stereochemistry where applicable. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl) and the like.

The term "$C_{2-6}$alkynyl" denotes groups formed from straight chain, branched, or mono- or poly-cyclic hydrocarbon groups having at least one triple bond. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and the like.

The term "$C_{1-6}$ alkoxy" denotes linear or branched oxy-containing radicals each having alkyl portions of 1 to 6 carbon atoms. Examples of alkoxy include methoxy, ethoxy, n-propoxy, iso-propoxy, n-butoxy, n-pentoxy t-butoxy and the like.

The term "arylene" denotes single, polynuclear, conjugated and fused divalent residues of aromatic hydrocarbons. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like.

The term "heterocyclyl" denotes mono- or poly-cyclic heterocyclyl groups containing at least one heteroatom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6 membered heteromonocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered heteromonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl.

The term "optionally substituted" denotes a group that may or may not be further substituted with one or more groups selected from oxygen, nitrogen, sulphur, $C_{1-4}$ alkyl, $C_{2-6}$ alkenyl, $C_{2-4}$ alkynyl, aryl, halo, halo $C_{1-4}$ alkyl, halo$C_{2-4}$alkenyl, halo$C_{2-4}$alkynyl, haloaryl, hydroxy, $C_{1-4}$alkoxy, $C_{2-4}$alkenyloxy, $C_{2-4}$alkynyloxy, aryloxy, carboxy, benzyloxy, halo$C_{1-4}$alkoxy, halo$C_{2-4}$alkenyloxy, haloalkynyloxy, haloaryloxy, nitro, nitro$C_{1-4}$alkyl, nitro$C_{2-4}$alkenyl, nitro$C_{2-4}$alkynyl, nitroaryl, nitroheterocyclyl, azido, amino, $C_{1-4}$alkylamino, $C_{2-4}$alkenylamino, $C_{2-4}$alkynylamino, arylamino, benzylamino, acyl, $C_{2-4}$alkenylacyl, $C_{2-4}$alkynylacyl, arylacyl, acylamino, acyloxy, aldehydro, $C_{1-6}$alkylsulphonyl, arylsulphonyl, $C_{1-6}$alkylsulphonylamino, arylsulphonylamino, alkylsulphonyloxy, arylsulphonyloxy, heterocyclyl, heterocycloxy, heterocyclylamino, haloheterocyclyl, $C_{1-4}$alkylsulphenyl, arylsulphenyl, carbo$C_{1-6}$alkoxy, carboaryloxy, mercapto, $C_{1-4}$alkylthio, arylthio, acylthio and the like.

Process

The polyurethanes of the present invention may be prepared by any technique familiar to those skilled in the manufacture of polyurethanes. These include one or two step procedures. The polymerisation can be carried out in conventional apparatus or within the confines of a reactive injection moulding or mixing machines.

In a one step procedure, the appropriate amounts of components (a) and (b) or (c) are mixed. The mixture is then cured. As described above, the mixture of components (a) and (c) may require the application of an external energy source such as UV radiation depending on the initiator employed.

The polyurethanes can also be prepared by a two step procedure where a prepolymer having terminally reactive polyisocyanate groups is prepared from component (b). The prepolymer is then reacted with component (a).

Additives

If desired, conventional polyurethane processing additives such as catalysts for example dibutyl tin dilaurate (DBTD), stannous oxide (SO), 1,8-diazabicyclo[5,4,0]undec-7-ene (DABU), 1,3-diacetoxy-1,1,3,3-tetrabutyldistannoxane (DTDS), 1,4-diaza-(2,2,2)-bicyclooctane (DABCO), N,N,N',N'-tetramethylbutanediamine (TMBD) and dimethyltin dilaurate (DMTD); antioxidants for example Irganox (Registered Trade Mark); radical inhibitors for example tris-nonylphenyl phosphite (TNPP); stabilisers; lubricants for example Irgawax (Registered Trade Mark); dyes; pigments; inorganic and/or organic fillers; and reinforcing materials can be incorporated into the biostable polymer during preparation. Such additives are preferably added in step (i) of the processes of the present invention up to 10% based on the total weight of gel, preferably up to 5%, more preferably 2% or less.

Medical Applications

The polyurethanes of the present invention are particularly useful in preparing biomaterials and medical devices, articles or implants.

The term "biomaterial" refers to a material which is used in situations where it comes into contact with the cells and/or bodily fluids of living animals or humans.

The medical devices, articles or implants may include soft tissue implants designed to replace and augment tissues including breast tissue, testicular tissue, cartilage, muscle and any connective tissue apart from teeth and bone such as the soft tissue implants disclosed in PCT/AU2006/001488; orthopaedic joints or parts thereof including spinal discs and small joints; bone suture anchors; reconstructive facial surgery; controlled drug release devices; components in key hole surgery; biosensors; tools and accessories for insertion of medical devices, infusion and flow control devices; and urethral, neurological or vascular bulking agents.

When the gel is used as a soft tissue implant it may be implanted using the method disclosed in PCT/AU2006/001488.

In the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

EXAMPLES

The invention will now be described with reference to the following non-limiting examples.

Physical Property Tests

Biological Stability:

The biological stability of the gels is achieved by the incorporation of large amount of silicon.

Rheology:

Both the natural feel and the form stability can be related to rheological factors. A good creep-recovery performance describes the feel or the elasticity. The parameters of storage modulus (G') and loss modulus (G") as measured in frequency sweep measurement on a rheometer describe the form stability. G'>G" at low frequencies ($0.01$ s$^{-1}$ to $1$ s$^{-1}$) implies form stability.

Procedure for Creep Recovery & Frequency Sweep Analysis:

The Creep Recovery is tested using Haake RheoStress 1 Rheometer. After the initialisation process under compressed air atmosphere, the parallel plates are subjected to zero point measurement. The sample is loaded and the gap position set. The excess sample is trimmed and is ready for the experiment.

The creep recovery analysis is carried out at 37° C. The sample is thermostated for 300s before the actual experiment starts to ensure temperature equilibrium. The experiment is carried at a force of 10 Pa for a duration of 60s and from the plot of J (1/Pa, compliance) Vs t(s), the creep recovery results can be obtained.

For frequency sweep measurement, after trimming the sample, the experiment was conducted at 37° C., with similar temperature equilibrating conditions. It is carried out in the frequency range of 0.01 Hz to 10 Hz. The frequency sweep provides about the structural conditions of the sample. It is possible to distinguish between a particle solution, an entangled solution (paste) and a three dimensional network (gel) simply by the shape of G', G" (Pa) and η* (Pa s) Vs f (Hz) curves.

Extractables:

The extractables in hexane as measured in the Soxhlet extraction technique over 24 hours shows an average value of around 50% for the silicone gels.

Extraction Procedure

The extraction procedure involved five pieces of apparatus: condenser, soxhlet extractor tube, extraction thimble, 250 mL round-bottom flask and a heating mantle. The procedure was carried out as follow:

Accurately weighed the 250 mL round bottom (R.B.) flask.
Poured approximately 160 mL of Hexane into the R.B. flask Placed a known amount of gel sample into the thimble and the thimble was placed in the soxhlet extractor tube.

The R.B. flask was adapted to the lower end of the soxhlet extractor tube and the condenser was adapted the top end of the tube.

The gel sample was allowed to reflux in Hexane for 22 hours.

At the end of the extraction period, the extractables in Hexane were collected in the R.B. flask.

Hexane was removed using rotary evaporator.

The R.B. flask containing the extractable residue was accurately weighed

The amount of extractable residue was calculated from the weight of the gel used for extraction.

The results were report as % weight loss.

Basic Strategy

The approaches used in the formulation of gels involve initiation of cross-linking by the use of various functionalities of the reactants including unsaturated or double bonds in the PDMS molecule and then making the double bond reactive by using a ultraviolet light source or other techniques.

Reactants used for Gel Synthesis

The reactants used for synthesizing the gels include a di-isocyanate in the form of MDI and different hydroxyl terminated polyols of functionalities varying from 1 to 3. The reactants are set out in Table 1 below:

TABLE 1

| Isocyanate | Methylene diphenylene isocyanate (MDI) |
|---|---|
| Silicon containing bi-functional macro-diol | bis(6-hydroxyethoxypropyl) polydimethylsiloxane (PDMS) of number average molecular weight (Mn) between 900-2100 |
| Tri-functional Polyols | A mixture of silicon containing polyols of different functionalities with an effective functionality of 3 A silicon containing polyol having an actual functionality of 3 |

Some of the above reactants are available commercially, however, the silicon-containing multifunctional polyols or polyisocyanates that are not available commercially have been synthesised in Examples A to F below.

Example A

T-Shape Triol

This example illustrates the preparation of hydroxyethoxypropyl terminated 9.09%-(hydroxyethoxypropyl methyl siloxane)(dimethyl siloxane) copolymer (Ia).

498.04 g of octamethylcyclotetrasiloxane ($D_4$), 0.62 g of 1,3,5,7-tetramethylcyclotetrasiloxane, and 1.34 g of TMDS were mixed in a glass bottle containing a magnetic stirrer bar. 0.64 g of trifluoromethanesulfonic acid was added to the mixture and the bottle sealed with an air tight cap. The mixture was stirred vigorously for 18 hours at room temperature after which 10 g of sodium carbonate was added. The bottle was resealed and stirred for 6 hours, after which the sodium bicarbonate was filtered off to give 500 g of hydride terminated (methylhydrosiloxane) (dimethylsiloxane) copolymer intermediate.

In a three-neck 2 L round bottomed flask equipped with a water cooled condenser equipped with a silica gel drying tube and a thermometer were placed with 500 g of the hydride terminated poly(methylhydrosiloxane) (dimethylsiloxane) copolymer and 357 mL of dry toluene. The mixture was heated, while stirring, to 60° C. 0.0015 g of Karstedt's catalyst was added to the mixture. 4.07 g of 2-allyloxyethanol was added drop wise to the mixture during which time the temperature of the mixture rose to 114° C. after which the reaction mixture was maintained at 70° C. for 1 hour. Silanic hydrogen content was checked by infrared spectroscopy. When no trace was detectable, the reaction was considered to be complete. The reaction mixture was allowed to cool to room temperature and treated with 20 g of activated carbon for 18 hours while stirring. The reaction mixture was filtered through celite to remove the carbon. The toluene was removed by rotary evaporator at 80° C. under a reduced pressure of 20 torr. The mixture was transferred to a Kugelrohr distillation apparatus and stripped of low molecular weight species at 100° C. under a reduced of $1 \times 10^{-1}$ torr to give 504.07 of hydroxyethoxypropyl terminated 9.09%-(hydroxyethoxypropyl methyl siloxane)(dimethyl siloxane) copolymer (Ia) as a colourless oil (MW 50001.07).

Example B

Tripod Triol

This example illustrates the preparation of $\alpha,\alpha',\alpha''$ (methylsilylidyne)tris-[ω[(hydroxyethoxypropyl-dimethylsilyl)oxy]poly(dimethylsilyene)]](9Cl) (IIa).

138.28 g of $D_4$ and 1.70 g of methyltris (dimethylsiloxy) silane were mixed in a glass bottle containing a magnetic stirrer bar. 0.006 g of trifluoromethanesulfonic acid was added to the mixture and the bottle sealed with an air tight cap. The mixture was stirred vigorously for 7 hours at room temperature after which 10 g of sodium bicarbonate was added. The bottle was resealed and stirred overnight, after which the sodium carbonate was filtered off to give 139.9 g of hydride terminated $\alpha,\alpha',\alpha''$-(methylsilylidyne)tris-[ω[(dimethylhydrosilyl)oxy]poly(dimethylsilyene)]](9Cl) intermediate.

In a three-neck 1 L round bottomed flask equipped with a water cooled condenser equipped with a silica gel drying tube, a 250-mL pressure compensating dropping funnel, and a thermometer were placed 139.9 g of the $\alpha,\alpha',\alpha''$-(methylsilylidyne)tris-[ω[(dimethylhydrosilyl)oxy]poly (dimethylsilyene)]](9Cl) intermediate and 250 mL of dry toluene. The mixture was heated, while stirring, to 70° C. 0.5 mL of a toluene solution of Karstedt's catalyst (containing 0.1 mmoles Pt/mL) was added to the mixture. 2.10 g of 2-allyloxyethanol was added drop wise to the mixture from the dropping funnel. The addition was made over a 45 minute period during which time the temperature of the mixture rose to 95° C. after which the reaction mixture was maintained at 70° C. for 1 hour. Silanic hydrogen content was checked by infrared spectroscopy. When no trace was detectable the reaction was considered to be complete. The reaction mixture was allowed to cool to room temperature and treated with 20 g of activated carbon for 18 hours whilst stirring. The reaction mixture was filtered through celite to remove the carbon. The toluene was removed by rotary evaporator at 80° C. under a reduced pressure of 20 torr. The pale yellow product was treated with 10 g of activated carbon for 3 days to remove the residual colour. The oil was filtered through celite to remove the carbon and then transferred to a Kugelrohr distillation apparatus and stripped of low molecular weight species at 140° C. under a reduced pressure of $1 \times 10^{-1}$ tor to give 142 g α,α',α''-(methylsilylidyne)tris-[ω[(hydroxyethoxypropyldimethylsilyl)oxy]poly(dimethylsilyene)]](9Cl) (IIa) as a colourless oil (MW 50000).

Example C

T-Shape Acrylate Macrodiol

This example illustrates the preparation of hydroxyethoxypropyl terminated 3.55%-(methyl-methacryloxypropyl methyl siloxane)(dimethyl siloxane) copolymer (Ib).

246.61 g of 1,3,5,7-tetramethylcyclotetrasiloxane, 0.37 g of $D_4$ and 3.01 g of α,ω-bis(hydroxyethoxypropyl) polydimethylsiloxane (MW 1943) were mixed in a glass bottle containing a magnetic stirrer bar. 0.314 g of trifluoromethanesulfonic acid was added to the mixture and the bottle sealed with an air tight cap. The mixture was stirred vigorously for 3.5 hours at room temperature after which 20 g of sodium bicarbonate was added. The bottle was resealed and stirred for overnight, after which the sodium carbonate was filtered off to give 250 g of hydroxyethoxypropyl terminated (methylhydrosiloxane) (dimethyl siloxane) copolymer intermediate.

In a three-neck 3 L round bottomed flask equipped with a water cooled condensed equipped with a silica gel drying tube and a thermometer were placed with 250 g of hydroxyethoxypropyl terminated (methylhydrosiloxane) (dimethyl siloxane) copolymer intermediate given above and 178.57 mL of dry toluene. The mixture was heated, while stirring, to 60° C. 0.0003 g of Karstedt's catalyst was added to the mixture. 0.9782 g of allylmethacrylate was added drop wise to the mixture. During the addition, the temperature of the mixture rose to 72° C. after which the reaction mixture was maintained at 70° C. for 18 hours. Silanic hydrogen content was checked by infrared spectroscopy. When no trace was detectable, the reaction was considered to be complete. The reaction mixture was allowed to cool to room temperature and treated with 20 g of activated carbon for 18 hours while stirring. The reaction mixture was filtered through celite to remove the carbon followed by filtration through a 0.2 μm Teflon filter. 0.0577 g of MEHQ was added to the toluene solution and then the toluene was removed by rotary evaporator at 60° C. under a reduced pressure of 20 torr. The mixture was transferred to a Kugelrohr distillation apparatus and stripped of low molecular weight species at 50° C. under a reduced pressure of $1 \times 10^{-1}$ torr for 20 minutes. This process was repeated 3 times to give 200.86 g of hydroxyethoxypropyl terminated 3.55%-(methylmethacryloxypropyl methyl siloxane) (dimethyl siloxane) copolymer (Ib) as a pale yellow oil (MW 161851.72).

Example D

T-Shape Triisocyanate

This example illustrates the preparation of isocyanate terminated (propyl methyl siloxane)(dimethyl siloxane) copolymer (Ic).

149.41 g of $D_4$, 0.18 g of 1,3,5,7-tetramethylcyclotetrasiloxane, and 0.40 g of TMDS were mixed in a glass bottle containing a magnetic stirrer bar. 0.1907 g of trifluoromethanesulfonic acid was added to the mixture and the bottle sealed with an air tight cap. The mixture was stirred vigorously for 24 hours at room temperature after which 5 g of sodium bicarbonate was added. The bottle was resealed and stirred for 24 hours, after which the sodium carbonate was filtered off through 0.5 μm filter paper under vacuum at room temperature to give 150 g of hydride terminated (methylhydrosiloxane) (dimethylsiloxane) copolymer intermediate.

In a three-neck 1 L round bottomed flask equipped with a water cooled condensed equipped with a silica gel drying tube and a thermometer were placed with 150 g of the hydride terminated poly(methylhydrosiloxane) (dimethylsiloxane) copolymer and 107.14 mL of dry toluene. The mixture was heated, while stirring, to 60° C. 0.0005 g of Karstedt's catalyst was added to the mixture. 0.99 g of allylisocyanate was added in drops. The reaction mixture was maintained at 60° C. for 2 hours. Absence of silanic hydrogen and intactness of isocyanate group were checked by infrared spectroscopy. When no trace of silanic hydrogen was detectable the reaction was considered to be complete. The reaction mixture was allowed to cool to room temperature. The reaction mixture was filtered through 0.2 μm filter paper under vacuum at room temperature. The toluene was removed by rotary evaporator at 80° C. under a reduced pressure of 20 torr to give 150.99 g of isocyanate terminated (propyl methyl siloxane) (dimethyl siloxane) copolymer (Ic) as a colourless oil (MW 25170.54).

Example E

Vinyl Siloxane Prepolymers

Vinyl siloxane prepolymers (Id)-(If) were prepared via acid-catalysed ring opening polymerization of either tetravinyl-tetramethyl cyclo tetra siloxane ($D^V_4$) or a mixture of tetravinyl-tetramethyl cyclo tetra siloxane ($D^V_4$) and octamethyl cyclo tetra siloxane ($D_4$) or a mixture of tetravinyl-tetramethyl cyclo tetra siloxane ($D^V_4$), octamethyl cyclo tetra siloxane ($D_4$) and hexamethyl disiloxane to prepare poly vinyl-methyl siloxane prepolymers.

The following examples illustrate the preparation of vinyl siloxane prepolymers.

The raw materials used in the following examples are:

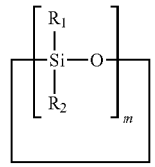 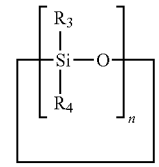

$D^V_4$ $R_1$ = Vinyl; $R_2$ = Methyl    D4: $R_3$ and $R_4$ = Methyl
m = 4                                    n = 4

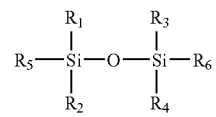

HMDS: $R_1$ to $R_6$ = Methyl

Example E1

50 g of $D^V_4$ was taken in glass bottle and mixed with 0.05 g of trifluoro sulfonic acid. The bottle was sealed with airtight cap and the mixture was stirred vigorously for 24 hours at room temperature, after which the reaction mixture was neutralized with 5 g of sodium bicarbonate and then kept for stirring for another ~16 hours. The sodium bicarbonate was then filtered off through 0.45μ filter paper under vacuum at room temperature. This was followed by a stripping step to remove the low molecular weight siloxane species from the vinyl siloxane prepolymers (Id).

Example E2

1.89 g of $D^V_4$ and 8.11 g of $D_4$ were taken in glass bottle and mixed with 0.01 g of trifluoro sulfonic acid. The bottle was sealed with airtight cap and the mixture was stirred vigorously for 24 hours at room temperature, after which the reaction mixture was neutralized with 5 g of Sodium bicarbonate and then kept for stirring for another ~16 hours. The sodium bicarbonate was then filtered off through 0.45μ filter paper under vacuum at room temperature. This was followed by a stripping step to remove the low molecular weight siloxane species from the vinyl siloxane prepolymers (Ie).

Example E3

22.44 g of $D^V_4$ and 18.46 g of $D_4$ and 100.10 g HMDS were taken in glass bottle and mixed with 0.07 g of trifluoro sulfonic acid. The bottle was sealed with airtight cap and the mixture was stirred vigorously for 24 hours at room temperature, after which the reaction mixture was neutralized with 5 g of Sodium bicarbonate and then kept for stirring for another ~16 hours. The sodium bicarbonate was filtered off through 0.45μ filter paper under vacuum at room temperature. This was followed by a stripping step to remove the low molecular weight siloxane species from the vinyl siloxane prepolymers (If).

Example F

T-Shape Triepoxysiloxane

This example illustrates the preparation of epoxy terminated (propoxy methyl siloxane) (dimethyl siloxane) copolymer (Ig).

248 g of $D_4$, 0.30 g of 1,3,5,7-tetramethylcyclotetrasiloxane, and 1.70 g of TMDS were mixed in a glass bottle containing a magnetic stirrer bar. 0.3194 g of trifluoromethanesulfonic acid was added to the mixture and the bottle sealed with an air tight cap. The mixture was stirred vigorously for 24 hours at room temperature after which 5 g of sodium bicarbonate was added. The bottle was resealed and stirred for 24 hours, after which the sodium carbonate was filtered off through 0.5 μm filter paper under vacuum at room temperature to give 250 g of hydride terminated (methylhydrosiloxane) (dimethylsiloxane) copolymer intermediate.

In a three-neck 1 L round bottomed flask equipped with a water cooled condenser equipped with a silica gel drying tube, a 250 mL pressure compensating dropping funnel and a thermometer were placed 250 g of the hydride terminated poly(methylhydrosiloxane) (dimethyl-siloxane) copolymer and 178.57 mL of dry toluene. The mixture was heated, while stirring, to 60° C. 0.0017 g of Karstedt's catalyst was added to the mixture. 5.1771 g of allyl gycidyl ether was added in drops. During the addition, the temperature of the mixture rose to 72° C. after which the reaction mixture was maintained at 70° C. for 3.5 hours. Absence of silanic hydrogen and intactness of isocyanate group were checked by infrared spectroscopy. When no trace of silanic hydrogen was detectable, the reaction was considered to be complete. The reaction mixture was allowed to cool to room temperature and treated with 20 g of activated carbon for 18 hours while stirring. The reaction mixture was filtered through celite to remove the carbon followed by filtration through a 0.2 μm Teflon filter. The reaction mixture was allowed to cool to room temperature. The reaction mixture was filtered through 0.2 μm filter paper under vacuum at room temperature. The toluene was removed by rotary evaporator at 60° C. under a reduced pressure of 20 torr. The mixture was then transferred to a Kugelrohr distillation apparatus and stripped of low molecular weight species at 75° C. under a reduced pressure of $1 \times 10^{-1}$ torr for 2 hours. This process was repeated 3 times to give 255.18 g epoxy terminated (propoxy methyl siloxane) (dimethyl siloxane) copolymer (Ig) as a colourless oil (MW 20046.98). Similarly, the above synthesis can be modified to prepare different possible end terminated disiloxane copolymers. Examples include, epoxy terminated (propoxy methyl siloxane) (pendant hydroxyethoxypropyl methyl siloxane) (dimethyl siloxane) copolymer (Ih), hydroxyethoxypropyl siloxane (pendant epoxy terminated (propoxy methyl siloxane)) (dimethyl siloxane) copolymer (Ii) and epoxy terminated (propoxy methyl siloxane) (pendant methylmethacryloxypropyl methyl siloxane) (dimethyl siloxane) copolymer (Ij).

Scheme 1

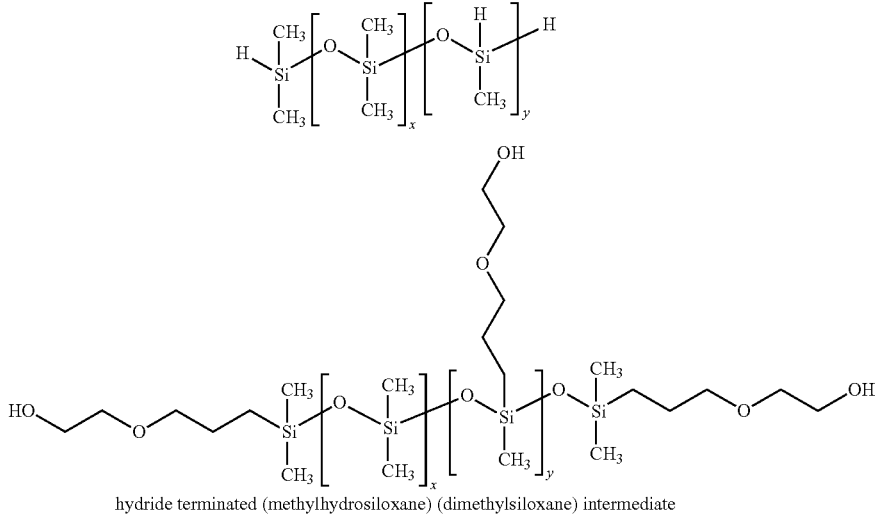

hydride terminated (methylhydrosiloxane) (dimethylsiloxane) intermediate

-continued

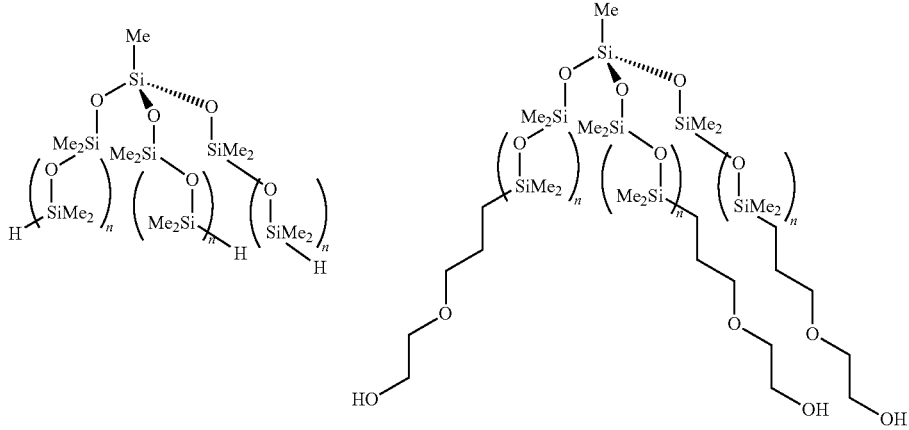

α, α', α''-(methylsilylidyne)tris-[ω[(dimethylhydrosilyl)oxy]poly(dimethylsilyene)]](9Cl) intermediate.

(Ib)

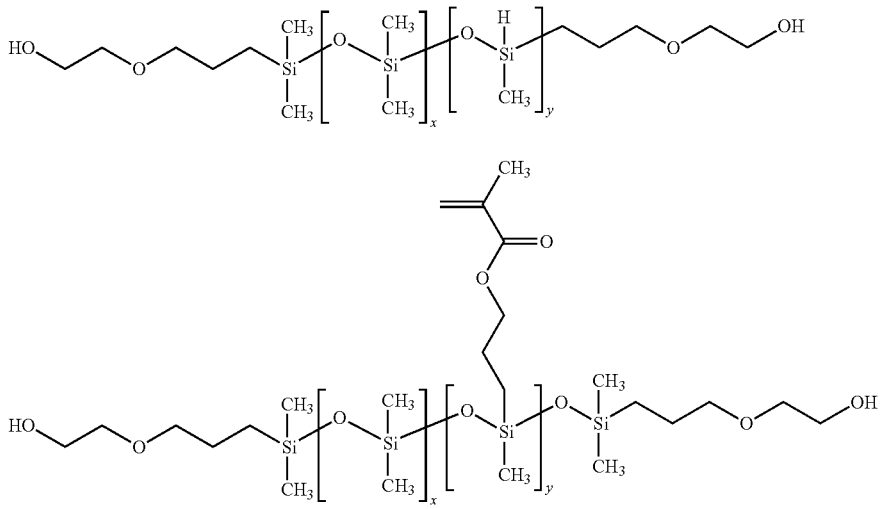

hydroxyethoxypropyl terminated (methylhydrosiloxane)(dimethyl siloxane) copolymer intermediate (Id)

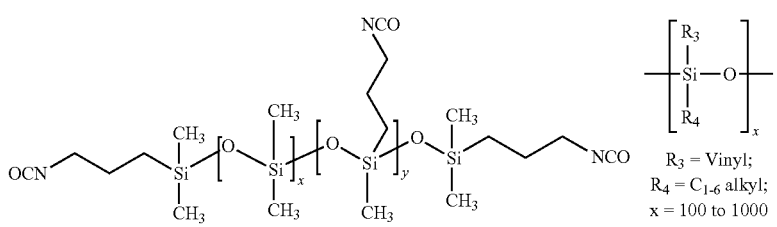

$R_3$ = Vinyl;
$R_4$ = $C_{1-6}$ alkyl;
x = 100 to 1000

(Ie)

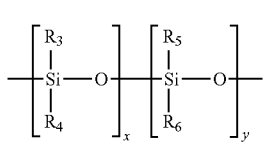

$R_1$ = Vinyl; $R_4$, $R_3$ and $R_6$ = $C_{1-6}$ alkyl; x = 100 to 1000 and y = 4 to 200

(If)

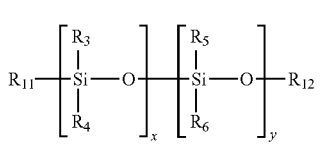

$R_3$ = Vinyl; $R_4$, $R_5$ and $R_6$ = $C_{1-6}$ alkyl; $R_{11}$ and $R_{12}$ = $C_{1-6}$ alkyl, hydroxyl, methoxy and/or ethoxy; x = 100 to 1000 and y = 4 to 200

-continued

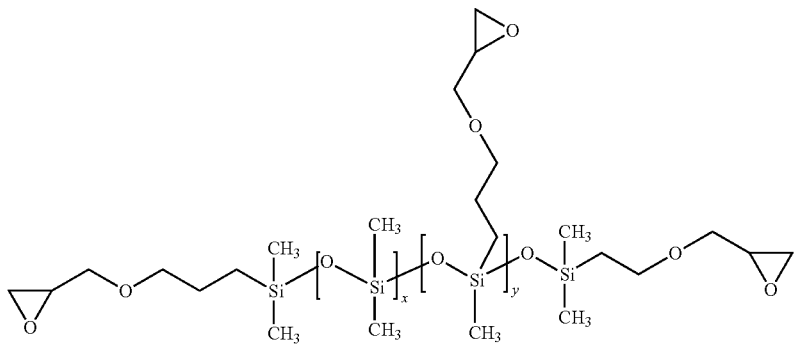
(Ig)

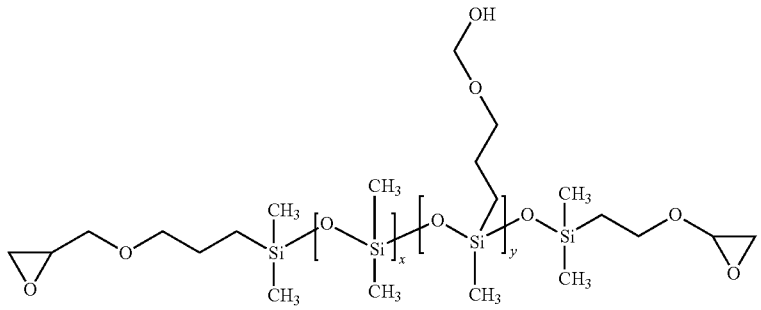
(Ih)

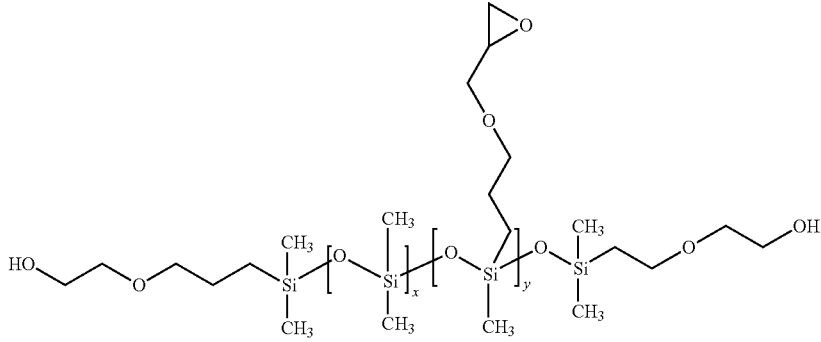
(Ii)

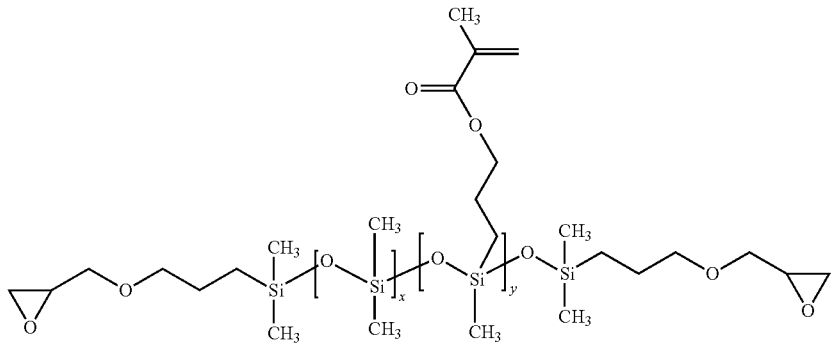
(Ij)

Gel Synthesis

The gels were synthesised using different processes:

One Shot Process—All reactants of the gel were added and mixed together.

Two Stage Slow Additive Process—The gel synthesis in this process occurred with the formation of a difunctional isocyanate terminated pre-polymer in the first stage followed by the addition of the hydroxyl terminated multifunctional polyols.

UV Curing—For the process of curing with ultra-violet light, a formulation containing an unsaturation in the polyol segment was prepared. A photoinitiator was added to the mixture and this in the presence of an externally supplied, long wavelength, ultraviolet radiation resulted in the formation of a cross linked gel.

Example 1

4,4'-Diphenylmethane diisocyanate (MDI) and synthesised hydroxyethoxypropyl terminated 9.09%-(hydroxyethoxypropyl methyl siloxane)(dimethyl siloxane) copolymer (T-Triol) (Ia) prepared in Example A were stirred for 5 min and cured.

The formulations of the components, stoichiometries are tabulated below.

| NCO/OH | MDI (g) | MW of T-Triol | Triol (g) |
|---|---|---|---|
| 1.0 | 0.40 | 20 000 | 21.59 |

A gel with good rheological properties was obtained.

Example 2

The synthesised T-shape trisiocyanate (Ic) prepared in Example D and siloxane polyols of varying molecular weight (1000, 2000) were stirred mechanically with and without catalyst for 5 min at room temperature and cured.

| NCO/OH | T Tri-isocyanate (g) | MW of T-tri-isocyanate | PDMS MW | PDMS (g) |
|---|---|---|---|---|
| 1.0 | 10 | 50000 | 2000 | 0.28 |
| 1.0 | 10 | 50000 | 1000 | 0.61 |

The synthesised gel was very elastic and had good rheological properties.

Example 3

The synthesised T-shape trisiocyanate (Ic) prepared in Example D and short chain diols (eg. butane diol) were stirred mechanically with and without catalyst for 5 min at room temperature and cured. In one example, 10 g of the T-shape triisocyanate was reacted with 0.027 g of BDO, the mixture stirred mechanically at room temperature for 5 minutes. The mixture cured at room temperature to a good elastic gel.

Example 4

Appropriate amount of synthesised T-shape acrylate macrodiol (Ib) prepared in Example C of varying MW (20,000-100,000) was accurately weighed in a Petri dish and mixed thoroughly using a spatula with required weight percentage (w/w) of different photoinitiators such as Irgacure 819, Irgacure 2022 (varying percentage from 0.25%-2% w/w) in ~1 ml of toluene and placed in the UV chamber (UV lamp, varying wavelength) to cure in few minutes. A good gel with softness varying as a function of the acrylate molecular weight was obtained.

Example 5

The gels were prepared in two steps; preparation of prepolymer by reacting a difunctional polyol with a diisocyanate to get desired NCO index (NCO/OH) followed by reaction of pre-polymer with synthesised hydroxyethoxypropyl terminated 9.09%-(hydroxyethoxypropyl methyl siloxane)(dimethyl siloxane) copolymer (T-shape Triol) (Ia) (MW 20,000-50,000) prepared in Example A.

Preparation of Prepolymer

The PDMS (MW 1000) was degassed at 70° C. under vacuum prior to synthesis. Molten MDI was placed in a three necked round bottom flask which was fitted with a mechanical stirrer and nitrogen inlet. The flask was placed in an oil bath set at 70° C. The degassed PDMS was added to MDI and was stirred by mechanical stirrer under a nitrogen atmosphere for 2 hours.

After completion of the addition of PDMS, the temperature of the oil bath was increased to 80° C. The prepolymer stirred at 100 rpm under nitrogen atmosphere for 2 h. The prepolymer was degassed for 1 hour under vacuum.

Reaction with Multifunctional Polyol

The prepolymer and T-shape triol (Ia) were stirred mechanically with and without catalyst for 5 min at room temperature and allowed to cure.

| Pre-polymer (g) | T-Triol Mwt. | T-Triol (g) | Catalyst (drops) |
|---|---|---|---|
| 2.75 | 20000 | 27.25 | — |
| 1.89 | 30000 | 28.11 | 1 |
| 1.44 | 40000 | 28.56 | 1 |
| 1.16 | 50000 | 28.84 | 1 |

Example 6

In another example using UV curing, the molten MDI was placed in a three necked round bottom flask which was fitted with a mechanical stirrer and nitrogen inlet. The flask was placed in an oil bath set at 60° C. The synthesised T-shape acrylate macrodiol (Ib) prepared in Example C of varying Mw 1000-100000) was added to MDI and stirred by mechanical stirrer under a nitrogen atmosphere for 2 h and was degassed for 1 h under vacuum. The chain extended polymer accurately weighed in a pedri dish and mixed thoroughly using a spatula with required weight percentage (w/w) of different photoinitiators such as Irgacure 819, Irgacure 2022 (varying percentage from 0.25%-2% w/w) in ~1 ml of toluene and placed in the UV chamber (UV lamp, varying wavelength) to cure in few minutes.

Example 7

Using one step procedure, 5 g of vinyl siloxane prepolymers I(d), I(e) and/or I(f) prepared in Example E are mixed with an initiator and cured with an external energy source such as UV radiation, thermal energy depending on the initiator employed. The photoinitiators employed include Irgacure 819, Irgacure 2020, Irgacure 2022 and Dragacure 1173. Free radical initiators employed include benzoyl peroxide and cumyl peroxide.

UV Curing:

For the process of curing with ultra-violet light, to 5 g of vinyl siloxane prepolymers a photoinitiator was added, mixed thoroughly and this in the presence of an externally supplied, long wavelength, ultraviolet radiation cured to a cross linked gel.

Thermal Curing:

For the process of temperature curing, to 5 g of vinyl siloxane prepolymers a free radical initiator was added, mixed thoroughly and this when cured in the oven maintained at 70° C. yielded a cross linked gel.

Example 8

The synthesised T-shape triepoxy siloxane (Id) prepared in Example F and diamine/HMWt. siloxane diamine were mechanically mixed for ~5 min at room temperature and cured in the oven at 70° C. A soft elastic gel with good rheological properties was obtained.

| MW of T-tri-epoxy siloxane | T Tri-epoxy siloxane (Moles) | Ethylene diamine/HMWt. Aminosiloxane MW | Ethylene diamine/HMWt. Aminosiloxane (Moles) |
|---|---|---|---|
| 20000 | 2 | 60.1 | 3 |
| 20000 | 2 | 248.52 | 3 |
| 20000 | 2 | 603.91 | 3 |

Example 9

Cytotoxicity Study Using the Iso-Elution Method

Purpose

To evaluate the biocompatibility of a test article extract using an in vitro mammalian cell culture test. This study is based on the requirements of the International Organization for Standardization 10993; Biological Evaluation of Medical Devices, Part 5: Tests for Cytotoxicity: in vitro Methods.

Ratio of Test Material to Extraction Vehicle:

Material thickness less than 0.5 mm—ratio of 60 $cm^2$:10 ml (based on the USP ratio 120 $cm^2$:20 ml)

Extraction Vehicles:

Single strength Minimum Essential Medium supplemented with 5% serum and 2% antibiotics (1×MEM)

Extraction Conditions:

The extraction conditions shall attempt to exaggerate the clinical use conditions so as to define the potential toxicological hazard; however, they should not in any instance cause physical changes such as fusion or melting, which results in a decrease in the available surface area. A slight adherence of the pieces can be tolerated.

Control Articles:

Negative Control: high density polyethylene, will be prepared based on a ratio of 60 $cm^2$:20 ml extraction vehicle. A single preparation of the material will be made and extracted at 37° C. for. 24 hours. Serial dilutions will be prepared for an end-point titration procedure.

*NOTE: The current positive control material has been qualified as an acceptable replacement for the USP recommended control material.

Test System and Justification:

Mammalian cell culture monolayer, L-929, mouse fibroblast cells, (ATCC CCL 1, NCTC Clone 929, of strain L, or equivalent source), will be used. In vitro mammalian cell culture studies have been used historically to evaluate cytotoxicity of biomaterials and medical devices (Wilsnack, et al., 1973).

Test System Management:

L-929, mouse fibroblast cells, (ATCC CCL 1, NCTC Clone 929, of strain L, or equivalent source) will be propagated and maintained in open wells containing single strength Minimum Essential Medium supplemented with 5% serum and 2% antibiotics (1×MEM) in a gaseous environment of 5% carbon dioxide ($CO_2$). For this study, 10 $cm^2$ wells will be seeded, labelled with passage number and date, and incubated at 37° C. in 5% CO to obtain confluent monolayers of cells prior to use. Aseptic procedures will be used in the handling of the cell cultures following approved Standard Operating Procedures.

Methods and Route of Administration:

Each culture well will be selected which contains a confluent cell monolayer. The growth medium in triplicate cultures will be replaced with 2 ml of the test extract. Similarly, triplicate cultures will be replaced with 2 ml of the reagent control, negative control extract and the undiluted and each titer of the positive control. Each well will be incubated at 37° C. in 5% $CO_2$ for 48 hours.

Following incubation, the cultures will be examined microscopically (100×) to evaluate cellular characteristics and percent lysis.

Evaluation Criteria and Statistics:

The confluency of the monolayer will be recorded as (+) if present and (−) if absent. In addition, the color of the test medium will be observed and compared to the negative control medium. Each culture well will be evaluated for percent lysis and cellular characteristics using the following criteria:

| Grade | Reactivity | Observations | |
|---|---|---|---|
| 0 | None | Discrete intracytoplasmic granules | No lysis |
| 1 | Slight | Not more than 20% of the cells are round, loosely attached, and without intracytoplasmic granules | Not more than 20% lysis |
| 2 | Mild | Not more than 50% of the cells are round and devoid of intracytoplasmic granules | Not more than 50% lysis. |
| 3 | Moderate | Not more than 70% of the cell monolayer contains rounded cells | Not more than 70% lysis |
| 4 | Severe | Nearly complete destruction of the cell monolayer | Greater than 70% lysis | single preparation of the material will be made, and will be extracted using the same conditions as described for the test article.

Reagent Control: A single aliquot of the extraction vehicle without test material will be prepared using the same conditions as described for the test article.

Positive Control: Current positive control material*, tin stabilized at polyvinylchloride, will be prepared based on a For the test to be valid, the reagent control and the negative control must have a reactivity of none (grade 0) and the positive control must be a grade 3 or 4. The test sample meets the requirements of the test if the biological response is less than or equal to grade 2 (mild). The test will be repeated if the controls do not perform as anticipated and/or if all three test wells do not yield the same conclusion.

References for Example 9

21 CFR 58 (GLP Regulations).

International Organization for Standardization 10993: Biological Evaluation of Medical Devices, Part 5: Tests for Cytotoxicity: in vitro Methods.

United States Pharmacopeia (USP), current edition.

Wilsnack, R. E., "Quantitative Cell Culture Biocompatibility Testing of Medical Devices and Correlation to Animal Tests" Rio materials, Medical Devices and Art/Icfal Organs 4 (1976): 235-261.

Wilsnack R. B., P. S. Meyer and 3.0. Smith, 'Human Cell Culture Toxicity Testing of Medical Devices and Correlation to Animal Tests,' Biomaterials, Medical Devices and Artificial Organs 1 (1973): 543-562.

Example 10

Sensitization Study in the Guinea Pig (Maximization Method)

Purpose of the Study:

The objective of the maximization test in the guinea pig is to identify the potential for dermal sensitization. The Magnusson and Kligman method has been effective in identifying a variety of allergies. This study will be based on the requirements of the International Organization for Stanardization 10993: biological Evaluation of Medical Devides, Part 10: Tests for Irritation and Sensization.

Test Article:

The sample will be prepared as follows:
1. Ratio of test article extraction vehicle:
   Material thickness less than 0.5 mm—ratio of 120 cm² 20 ml
2. Extraction vehicle:
   0.9% sodium chloride USP solution (SC)
   cottonseed oil, NF (CSO)
3. Extraction condition:
   37° C., 72 hours (±2 hours)

Control Article:

The vehicle used to prepare the extract will be prepared in the same manner as the extract (but without test article) serve as the control measure. Untreated skin will serve as an additional control reference for scoring dermal reactions during the challenge phase.

Test System:

| | |
|---|---|
| Species: | Guinea pig (*Cavia porcellus*) |
| Strain: | Crl: (HA) BR |
| Source: | Charles River Laboratories |
| Sex: | No particular gender is prescribed for this test. If females are used) they will be nulliparous and not pregnant. |
| Body Weight Range: | 300-500 grams at identification |
| Age: | Young adults |
| Acclimation Period: | Minimum 5 days |
| Number of Animals: | 15 (per extract) |
| Identification Method: | Ear punch |

Justification of Test System:

The Hartley albino guinea pig has been used historically for sensitization studies (Magnusson and Kilgman, 1970). The guinea pig is believed to be the most sensitive animal model for this type of study. The susceptibility of the Hartley strain to a known sensitizing agent, 1-chloro-2,4-dinitrobenzene (DNCB) has been substantiated with this method.

Test and Control Article Preparation:

Fresh extracts will be prepared at each phase of the study as previously indicated (see Test Article). If the test material is suitable for patching, a topical application of the test sample (2 cm×2 cm patch) will be used at the challenge. The vehicle used to prepare the extract will be prepared in the same manner as the extract (but without test article) to serve as the control measure.

Methods and Route of Administration:

The day prior to treatment, 15 guinea pigs per extract (10 test, 5 control) will be weighed and identified. The fur from the dorsoscapular area of the animals will be removed with an electric clipper.

Induction I:

Three pair of intradermal injections will be administered to the animals within an approximate 2 cm×4 cm area the dorsoscapular region as follows:

Control Animals:
a. 0.1 ml of 50:50 (v/v) mixture of Freund's Complete Adjuvant (FCA) and the chosen vehicle
b. 0.1 ml of vehicle
c. 0.1 ml of a 1:1 mixture of the 50:50 (v/v) FCA and the vehicle Test Animals:
a. 0.1 ml of 50:50 (v/v) mixture of FCA and the chosen vehicle
b. 0.1 ml of test extract
c. 0.1 ml of a 1:1 mixture of the 50:50 (v/v) FCA and the test extract To minimize tissue sloughing the 'a' and "c' injections will be slightly deeper than "b'. Site 'c' will be injected slightly more caudal than site 'b".

Induction II:

Six days later, the injection sites will be clipped free of fur again and treated with 0.5 to 1 g of a 10% (w/w) sodium lauryl sulfate (SLS) suspension prepared by mixing the powdered SLS with petrolatum. The day following the SLS treatment, any remaining SLS residue will be gently wiped from the area with gauze.

A 2 cm×4 cm filter paper patch (3 mM, Whatman), saturated with 0.3 ml of the extract preparation or vehicle, will be applied over the same injection area and secured with a nonreactive tape. The trunk of each animal will then be wrapped snugly with an elastic band for 48 hours (±2 hours).

Challenge:

At 13 days after unwrapping induction II wraps, the fur will be clipped from the sides and flanks of all guinea pigs. On the following day, a nonwoven cotton disk backed by a flexible chamber (e.g. Hill Top Chamber®) and semiocclusive hypoallergenic tape, will be saturated with 0.3 ml of freshly prepared test material extract and applied to the right flank or dorsum of each animal. In addition, the vehicle control will be patched to the left flank or dorsum of each animal. An approximate 2 cm×2 cm section of test material itself (if appropriate) will be applied to the right flank.

The trunk of each animal will be wrapped for 24 hours (±2 hours). At patch removal the sites will be wiped with gauze. At 24 hours (±2 hours) after patch removal, the challenged sites and surrounding area will be shaved. The sites will be examined for signs of ahy irritation or sensitization reaction, as indicated by erythema and edema at a minimum of 2 hours and a maximum of 4 hours following the shave and at 48 (±2 hours) and 72 (±2 hours) hours after removal of the dressings. Prior to scoring, each site will be wiped gently with a 35% isopropyl alcohol gauze sponge.

Should the original challenge results prove to be equivocal, the animals may be rechallenged with a fresh test extract and vehicle control approximately 7 days after the first challenge patch application. The rechallenge will be conducted in the same manner as the challenge but at virgin sites on the opposite flank. After the test is completed, all animals will be handled in accordance with approved procedures.

Evaluations and Statistics:

Daily challenge scores for reactions will be recorded at 24, 48 and 72 hours after patch removal in accordance with the following Table:

| ERYTHEMA (ER) | | EDEMA (ED) | |
|---|---|---|---|
| Reaction | Numerical Grading | Reaction | Numerical Grading |
| No erythema | 0 | No edema | 0 |
| Slight erythema | 1 | Slight edema | 1 |
| Well-definded erythema | 2 | Well-defined edema | 2 |
| Moderate erythema | 3 | Moderate edema | 3 |
| Severe erythema to slight eschar formulation | 4 | Severe edema | 4 |

Any other observation relating to the site will be footnoted.

The responses will be compared within the test animal group and between test and control conditions. Control conditions are (~1) the vehicle control solution on the test animals and (2) the test extract, control solution and biomaterial (if applied) on the control animals.

In the final analysis of data, consideration will be given to the overall pattern, intensity, duration, and character of reactions of the test as compared to the control conditions. Statistical manipulation of data is not applicable to this study. An effect interpreted as "irritation" is generally observed at 24 hours, but diminishes thereafter, and is also concurrently present as a transient response in the control animals. Closed patches typically show maximal sensitization readings 48 to 72 hours after patch removal in the test condition but not in the control condition. Grades of 1 or greater in the test group generally indicate sensitization, provided that grades of less than 1 are observed on the control animals. If grades of 1 or greater are noted on control animal then the reactions of test animals which exceed the most severe control reaction are considered to be due to sensitization.

Background or artifactual reactions (e.g., from fur clipping, patch chamber edge, nonspecific FCA effects) will not be considered as evidence of a sensitization response. The treatment with FCA and occlusive dressings may lower the threshold level for skin irritation.

If the test group has a greater number of animals showing responses that are not greater than the control animals, a rechallenge may be conducted. The rechallenge will be conducted approximately 7 days after the first challenge at virgin sites on the opposite flank of the animals. Absence of dermal response at rechallenge may nullify earlier findings. Recurring observations in at least one of the same animals verify earlier findings.

References for Example 10

21 CFR 58 (GLP Regulations).
Guide for the Care and Use of Laboratory Animals, Institute for Laboratory Animal Research, National Academy of Sciences (Washington: National Academy Press, 1996).
International Organization for Standardization 10993: Biological Evaluation of Medical Devices, Part 10: Tests for Irritation and Sensitization.
Magnusson, B. and A. Kligman, Allergic Contact Dermatitis in the Guinea Pig (Springfield: C. H. Thomas, 192Q)
OLAW, Public Health Service Policy on Humane Care and Use of Laboratory Animals (NIH Publication)
United States Code of Federal Regulation (CFR) 9: The Animal Welfare Act.

Example 11

Acute Intracutaneous Reactivity Study in the Rabbit

Purpose:

The objective of this study is to evaluate the local dermal irritant effects of leachables extracted from the test article following intracutaneous injection in rabbits. This study will be based on the requirements of the International Organization for Standardisation 10993: Biological Evaluation of Medical Devices, Part 30: Tests for Irritation and Sensitization.

This study will be conducted in accordance with the Detailed information of the FDA Good Laboratory Practice (GLP) Regulations, 21CFR 58.

Test Article:

The sample will be prepared as follows:
1. Ratio of test article to extraction vehicle:
   Material thickness less than 0.5 mm—ratio of 120 $cm^2$; 20 ml.
3. Extraction vehicle: 0.9% sodium chloride USP solution (SC).
4. Extraction conditions: 37° C., 72 hours (±2 hours)

Control Article:

Reagent controls (extraction vehicle without test material) will be prepared in the same way and at the same time as the test extracts.

Test System:

| Species: | Rabbit (*Oryctolagus cuniculus*) |
|---|---|
| Strain: | New Zealand White |
| Source: | Single USDA licensed supplier |
| Sex: | No particular gender is prescribed in this test |
| Body Weight Range: | 2.0 kg or greater at selection |
| Age: | Young adults |
| Acclimation Period: | Minimum 5 days |
| Number of Animals: | Three per pair of extracts |
| Identification Method: | Ear tag |

Justification of Test System:

The intracutaneous injection test in rabbits is specified in the current ISO testing standards and has been used historically to evaluate biomaterial extracts.

Methods and Route of Administration:

The day prior to treatment, each rabbit will be weighed and clipped free of fur from the back and both sides of the spinal column to yield a sufficient injection area. The clipped area of the back will be wiped with a 70% alcohol soaked gauze pad just before injection and allowed to dry. Due to concern with the crowding and subsequent obscuring of injection sites, the test and control sites will not be cranial and caudal on the same side of the back as defined in the ISO standards. Each test extract will be administered in five intracutaneous injections of 0.2 ml each on the right side of each rabbit's back. Five reagent control injections will be injected similarly on the left side of the back. No more than two test extracts and the corresponding reagent controls will be injected into each animal. Injections will be about 2 cm apart. The appearance of the injection sites will be noted immediately after injection.

Observations for erythema and edema will be noted for each injection site at 24 (+2 hours), 48 (±2 hours) and 72 (±2 hours) hours after injection. Reactions will be scored on a 0 to 4 basis. Other adverse changes at the injection sites will also be noted. After the test is completed, all animals will be handled in accordance with approved procedures. The reactions will be evaluated according to the subjective rating scale as shown below:

| ERYTHEMA (ER) | EDEMA (ED) |
|---|---|
| 0 No erythema | 0 No edema |
| 1 Very-slight erythema (barely perceptible) | 1 Very-slight edema (barely perceptible) |
| 2 Well-defined erythema | 2 Well-defined edema (edges of area well-defined by definite raising) |
| 3 Moderate erythema | 3 Moderate edema (raised approximately 1 mm) |
| 4 Severe erythema (beet redness) to eschar formation preventing grading of erythema) | 4 Severe edema (raised approximately 1 mm, and extending beyond exposure area) |

Evaluations and Statistics:

No statistical analysis of the data will be performed. For each animal, the erythema and edema scores obtained at each time interval will be added together and divided by the total number of observations. This calculation will be conducted separately for each test extract and reagent control. The score for the reagent control will be subtracted from the score for the test extract to obtain the Primary Irritation Score. The Primary Irritation Score of each animal will be added together and divided by the total number of animals. The value obtained is the Primary Irritation Index (PII). The Primary Irritation Index is characterized by number and description as follows: 0-0.4 (negligible), 0.5-1.9 (slight), 2.0-4.9 (moderate), 5.0-8.0 (severe). If the response in the initial test is equivocal, additional testing may be necessary. Any adverse reaction noted in the test extract will be compared to the corresponding reagent control.

Report:

The final report will include a description of the methods employed, individual dermal scores for each test and control injection site, and the assessment of the results (Primary Irritation Scores and the Primary Irritation Index).

Records:

Test article and reagent control preparation data, dates of relevant activities (such as the study initiation and completion), the appearance of each injection site immediately after injection, individual dermal scores at 24, 48 and 72 hours, the Primary Irritation Score, and the Primary Irritation Index will be recorded.

References for Example 11

21 CFR 58 (GLP Regulations).
*Guide for the Care and Use of Laboratory Animals*, Institute for Laboratory Animal Research, National Academy or Sciences (Washington: National Academy Press, 1996).
International Organization for Standardization 10993: Biological Evaluation of Medical Devices, Part 10: Tests for Irritation and Sensitization.
OLAW, Public Health Service Policy on Humane Care and Use of Laboratory Animals.
United States Code of Federal Regulation (CFR) 9: The Animal Welfare Act.
United States Pharmacopeia (USP), current edition.

Example 12

USP and ISO Systemic Toxicity Study Extract

Purpose:

The objective of this study is to evaluate acute systemic toxicity of leachables extracted from the test article following a single intravenous or intraperitoneal injection in mice. This study will be conducted in accordance with the methods recommended by the International Organization for Standardization 10993: Biological Evaluation of Medical Devices, Part II: Tests for Systemic Toxicity.

Test Article:

The sample will be prepared as follows:
1. Ratio of test article to extraction vehicle:
   Material thickness less than 0.5 mm—ratio of 120 $cm^2$:20 ml
   Material thickness greater than or equal to 0.5 mm ratio of 60 $cm^2$:20 ml
   Irregularly shaped objects and/or sponsor option—ratio of 4 g:20 ml
2. Extraction vehicles:
   0.9% sodium chloride USP solution (SC)
   alcohol in saline 1:20 solution (AS)
   polyethylene glycol 400 (PEG)*
   vegetable oil
   Note: Due to the known pH of these vehicles, the pH of the test article extracts will not be determined.
   *If PEG is used, the PEG test extract and reagent control will be diluted with saline to obtain 200 mg of PEG/ml.
3. Extraction conditions:
   121° C., 1 hour
   70° C., 24 hours
   50° C., 72 hours
   37° C., 72 hours Control Article:

Blank controls (extraction vehicle without test material) will be prepared in the same way and at the same time as the test extracts.

Test System:

| Species: | Mouse (*Mus musculus*) |
|---|---|
| Strain: | Outbred albino |
| Source: | approved supplier |
| Sex: | No particular gender is prescribed for this test |
| Body Weight Range: | 17-23 grams at injection |
| Age: | No particular age is prescribed for this test |
| Acclimation Period: | Minimum 1 day |
| Number of Animals: | Five per extract and control |
| Identification Method: | Ear punch |

Justification of Test System:

Mice have historically been used to evaluate biomaterial extracts. The use of albino mice injected with a single intravenous (iV) or intraperitoneal (IP) dose of test article extract or control blank have been suggested by the current USP and ISO for evaluation of medical plastics.

Methods and Route of Administration:

Prior to dosing, the mice will be identified and weighed. Five animals will each be injected with the appropriate test extract at a dose of 50 ml/kg (SC, AS, vegetable oil) or 10 g/kg (PEG). Five mice will be similarly injected with the corresponding extraction vehicles. The SC and AS will be injected intravenously via the lateral tail vein while the PEG and vegetable oil will be injected intraperitoneally.

Mice will be observed for adverse reactions immediately after dosing, and at 4, 24, 48 and 72 hours after injection. Following the 72 hour observation, the animals will be weighed. Any animal found dead will be subjected to a gross necropsy of the viscera. After the test is completed, all animals will be handled in accordance with approved procedures.

Evaluations and Statistics:

No statistical analysis of the data will be performed. If during the observation period none of the mice treated with the test extract show a significantly greater reaction than the corresponding control mice, then the test sample meets the test requirements. If two or more mice die, or if abnormal behavior such as convulsions or prostration occurs in two or more mice, or if body weight loss greater than 2 grams occurs in three or more mice, the test sample does not meet the test requirements.

If any mice treated with the test extract show only slight signs of toxicity and not more than one mouse shows gross signs of toxicity or dies, a ten mouse retest may be required. If all ten mice treated with the test extract on the repeat test show no significant reaction greater than the control mice, then the test sample meets the current test requirements.

Report:

The final report will include a description of the methods employed, individual body weights, and any observations.

Records:

Test article preparation, dates of relevant activities (such as the study initiation and completion), initial and final body weights, and observations will be recorded.

References for Example 12

21 CFR 58 (GLP Regulations).
*Guide for the Care and Use of Laboratory Animals*, Institute for Laboratory Animal Research, National Academy of Sciences (Washington: National Academy Press, 1996).
International Organization for Standardization 10993: Biological Evaluation of Medical Devices, Part 11: Tests for Systemic Toxicity.
OLAW, Public Health Service Policy on Humane Care and Use of Laboratory Animals (NIH Publication).
United States Pharmacopeia (USP), current edition.

Example 13

Rat Subchronic Intraveneous Toxicity Study

Purpose:

The objective of this study is to evaluate the subchronic systemic toxicity of leachables extracted from the test article following repeated intravenous injections in rats for a period of 14 consecutive days.

Test Article:
1. Ratio of test article to extraction vehicle:
   Material thickness less than 0.5 mm—ratio of 120 $cm^2$:20 ml
   Material thickness greater than or equal to 0.5 mm—ratio of 60 $cm^2$:20 ml
   Irregularly shaped objects and/or sponsor option—ratio of 4 g:20 ml
2. Extraction conditions:
   121° C., 1 hour
   70° C., 24 hours
   50° C., 72 hours
   The extracts will be used within 24 hours of completion of the extraction process or as directed by the sponsor.

Control Article:

A vehicle control (SC without test article) will be prepared in the same way and at the same time as the test extract. A single group of common control animals may be dosed when multiple test articles are evaluated at the same time.

Test System:

| | |
|---|---|
| Species: | Rat (*Rat us norvigicus*) |
| Strain: | Hla ®: (SD)CVF ® |
| Source: | Hilltop Lab Animals, Inc. |
| Sex: | Ten male, ten female |
| Body Weight Range: | No particular weight range is prescribed for this study, however, individual pretreatment body weights will be within 20% of the group mean for each sex |
| Age: | Approximately 6 to 8 weeks old at first treatment |
| Acclimation Period: | Minimum 5 days |
| Number of Animals: | Twenty |
| Identification Method: | Ear punch or tag |

Methods and Route of Administration:

No more than one day prior to the first dose, rats will be weighed and randomly assigned to each treatment group. Ten rats (five male, five female) will receive an injection of the test article extract once each day for 14 consecutive days. The test extract will be injected via the lateral tail vein at a dose of 10.0 ml/kg. The individual daily dose will be based on the weight of each animal on the first dose day of each week. The appropriate dose volume will be calculated to the nearest 0.1 ml. An appropriate gauge needle attached to a disposable syringe will be used to deliver the injection. The injection rate will be approximately 1.0 ml/10 seconds. Animals will be dosed at approximately the same time each day. Ten rats (five male, five female) will be similarly injected with the control blank. The first day of dosing will be designated as day 1.

Laboratory Observations:
1. Animals will be observed daily for general health. Rats will also be observed for any adverse reactions immediately after injection.
2. Detailed examinations for clinical signs of disease or abnormality will be conducted at randomization and on days 8 and 15.
3. Body weights will be recorded to the nearest whole gram prior to the first dose, on day 8, 14 (pre-fasted weight) and 15 (fasted weight).
4. In the event of mortality, the following contingencies will apply:
   a. Should any animal die during the study, a macroscopic examination of the viscera will be conducted. Because of rapid postmortem tissue changes in small rodents, no final body weight or blood collection will be attempted. The organs and tissues designated in the Terminal Procedures portion of this protocol will be collected and fixed for histopathologic evaluation. The number of days the animal was on test will be considered in the final evaluation.

b. Should any animal exhibit adverse clinical signs or suffer from cage injury that for humane reasons necessitates euthanasia, it will be subject to the Terminal Procedures. The number of days the animal was on test will be considered in the final evaluation.

Terminal Procedures:

At the end of the workday on day 14, the animals will be weighed and food will be withheld for a maximum of 20 hours. On day 15, the animals will be weighed and then anesthetized by intraperitoneal injection of ketamine hydrochloride and xylazine (88 mg/kg+12 mg/kg) dosed at 3.0 ml/kg. The abdomen will be opened and a blood specimen will be collected from the posterior vena cava. The blood specimens will be forwarded to a contract laboratory for complete blood cell count with differential and clinical chemistry analyses. Rats will be euthanized by exsanguination while anesthetized.

Following exsanguination, a macroscopic observation of the viscera will be conducted. The following organs will be removed: heart, lungs, liver, spleen, thymus, kidneys (2), adrenal glands (2), mesenteric lymph nodes, submandibular lymph nodes, gonads (2) and any tissue with visible gross lesions. The liver, spleen, thyrnus, kidneys, adrenal glands and gonads will be weighed. Paired organs will be weighed together. The tissues will be preserved in 10% neutral buffered formalin (NBF) until further processing. The carcasses will be discarded.

After fixation, the tissues will be histologically processed (embedded, sectioned and stained in hematoxylin and eosin) for microscopic evaluation by a qualified pathologist.

Evaluation and Statistics:

Body weight data, organ weight data, organ/body weight ratios, hematology and clinical chemistry data will be evaluated statistically. Pre-fasted body weights will be used to determine weight gain and the fasted body weights will be used to determine anesthetic dosages at termination and organ/body weight ratios. Descriptive statistics and group comparisons of data will be accomplished using a validated statistical software package. After screening the data for normality and equal variance, the appropriate parametric or nonparametric tests will be performed. Normally distributed data with equal variance will be considered parametric and evaluated using an "unpaired t-test" for comparison of two groups. Jf data is nonparametric, the "Mann-Whitney Rank Sum Test" is used for two group comparisons. The data to be analyzed will include: body weight, organ weight and hematological parameters. The treatment groups will be used as variables. Calculations resulting in probability (p) values less than 0.05 will be considered statistically significant. If directed by the evaluating pathologist, statistical evaluation of pathologic findings may be conducted.

Clinical signs of systemic illness or death will not be analyzed statistically unless a rationale (such as frequently observed clinical signs or emergence of a pattern) for such analysis is apparent from these data. If the incidence of occurrence of any one or more observations is sufficient to warrant analysis, a chisquare test will be employed.

Data from male and female rats for body weights will be analyzed separately until and unless a rationale exists for combining the sexes. Body weight data will be expressed as absolute values. Data from male and female rats for hematology parameters will be analyzed separately unless a rationale exists for combining the sexes. In the event of statistical significance for any hematologic parameter, the results will be compared to a reference range to aid in determining biological significance.

Report:

The final report will include a description of the methods employed, clinical observations, body weight data, hematology and clinical chemistry data, organ weight data, organ/body weight ratios, necropsy findings, the microscopic evaluation in the histopathology report, the statistical analyses and conclusions.

References for Example 13

21 CFR 58 (GLP Regulations).

Guide for the Care and Use of Laboratory Animals, Institute for Laboratory Animal Research, National Academy of Sciences (Washington: National Academy Press, 1996).

ISO 10993-11. Biological Evaluation of Medical Devices, Part 11: Tests for Systemic Toxicity.

OECD Guideline for Testing of Chemicals, Repeated Dose Oral Toxicity—Rodent: 28-day or 14-day Study, Document Number 407.

OLAW, Public Health Service Policy on Humane Care and use of Laboratory Animals (NIH Publication).

Example 14

Genotoxicity: Bacterial Reverse Mutation Study

Purpose of the Study:

The purpose of the study is to evaluate whether an extract of the test material or a solubilized material will cause mutagenic changes in a tryptophan-dependent strain of *Escherichia coli* or in one or more strains of histidine-dependent *Salmonella typhimurium* in the presence or absence of 59 metabolic activation. The Bacterial Reverse Mutation Study will be used as a rapid screening procedure for the determination of inutagenic and potential carcinogenic hazards and should be used in conjunction with other tests that characterize potential genotoxicity properties. This study will be based on OECD guidelines and the requirements of the International Organization for Standardization: Biological Evaluation of Medical Devices—Part 3: Tests for Genotoxicity, Carcinogenicity and Reproductive Toxicity.

Test Article:

The sample will be prepared as follows:

Test article form:

Soluble material (solid or liquid)—complete "Preparation of Soluble Material"

Insoluble material—complete "Preparation of Extract"

Preparation of Extract (for Insoluble Materials):

1. Ratio of test material to vehicle:

Material thickness less than 0.5 mm, use ratio of 120 $cm^2$:20 ml

Material thickness greater than or equal to 0.5 nun, use ratio of 60 $cm^2$:20 ml Irregularly shaped objects and/or sponsor option, use ratio of 4 g:20 ml 2. Vehicle:
   0.9% Sodium Chloride for Injection, USP
   Dimethyl sulfoxide (DMSO)*
   95% ethanol (EtOH)**

*Dimethyl sulfoxide can be extracted at 37° C. for 72 hours, 70° C. for 24 hours or 50° C. for 72 hours.

**95% ethanol can only be extracted at room temperature (various times can be used).

3. Conditions (use highest temperature that will not degrade material);
   121° C., 1 hour
   70° C., 24 hours
   50° C., 72 hours
   37° C., 24 hours
   room temperature, 72 hours Preparation of Soluble Material:

1.—Solid:
   One gram of the sample will be transferred to a 10 ml volumetric flask. Various sized flasks may be used to accommodate nature of test material utilizing 100 mg/ml or 10% w/v. Appropriate vehicle (specified below) will be added (q.s.) to the 10 ml (or appropriate) demarcation to achieve 100 mg/ml or a 10% (w/v) solution of the material.

2.—Liquid:
   One milliliter of the sample will be transferred to a 10 ml volumetric flask. Various sized flasks may be used to accommodate nature of test material utilizing 100 mg/ml or 10% v/v. Appropriate vehicle (specified below) will be added (q.s.) to the 10 ml (or appropriate) demarcation to achieve 100 mg/ml or a 10% (v/v) solution of the material.

NOTE: GLP regulations 21 CFR 58.113 requires concentration analysis and stability determination for mixtures with carriers.

Vehicles:
   0.9% Sodium Chloride for Injection, USP
   Dimethyl sulfoxide (DMSO)
   95% ethanol (EtOH)

All preparations of soluble materials will be performed the day of test. In the event the material does not completely dissolve at these concentrations, serial dilutions will be prepared. The highest possible concentration that achieves complete dissolution of the material will be used for testing purposes.

Test System:
   Each *S. typhimurium* tester strain contains a specific mutation in the histidine operon and other mutations that increase their ability to detect mutagens. The *E. coli* strain contains a mutation in the tryptophan operon and a deletion in the uvrA gene. These genetically altered *S. typhimurium* strains (TA9S, TA100, TA1535, and TA1537) and *E. coli* strain (WP2uvrA) cannot grow in the absence of histidine or tryptophan, respectively. When placed in a histidine-free (for *S. typhimurium*) or tryptophan-free (for *E. coli*) medium, only those cells which mutate spontaneously back to their wild type state (histidine independent by manufacturing their own histidine, or tryptophan independent by manufacturing their own iryptophan) are able to form colonies. The spontaneous mutation rate (or reversion rate) for any one strain is relatively constant, but if a mutagen is added to the test system, the mutation rate is significantly increased.

| Tester Strain | Mutations/Genotypic Relevance |
|---|---|
| *S. typhimurium* TA98 | hisD3O52, rfa, uvrB, frameshift, pKM101 |
| *S. typhimurium* TA 1OO | hisG46, rfa, uvrB, missense, pKM101 |
| *S. typhimurium* TA 1535 | hisG46, rfa, uvrB, missense |
| *S. typhimurium* TA 1537 | hisC3O76, rfa, uvrB, frameshift |
| *E. coli* WP2uvrA | trpE65, uvrA, missense | rfa = causes partial loss of the lipopolysaccharide wall which increases permeability of the cell to large molecules (i.e., crystal violet inhibition)
uvrB or uvrA = deficient DNA excision - repair system (i.e., ultraviolet sensitivity)
frameshift = base-pair addition/deletion
missense = base-pair substitution
pKM101 = plasmid confers ampicillin resistance (R-factor) and enhances sensitivity to mutagens Metabolic Activation:
   Aroclor 1254—induced rat liver (s9 homogenate) will be used as metabolic activation. The material is prepared from male, Sprague Dawley rats. The rats are induced with one intraperitoneal injection of Aroclor 1254 (500 mg/ml) 5 days prior to sacrifice. The S9 homogenate is purchased from Organon Teknika Corporation, Box 15969, Durham, N.C. 27704-0969. Just prior to use, the S9 homogenate will be mixed with a buffer containing 0.4 M $MgCl_2$/65 M KCl, 1.0 M Glucose-6-phosphate, 0.1 M NADP, 0.2 M sodium phosphate buffer and sterile water.

Preparation of Tester Strains:
   Cultures of *Salmonella typhimurium*, TA98, TA100, TA1535 and TA1537, and *Escherichia coli*, WP2uvrA, will be inoculated to individual Erlenmeyer flasks containing oxoid broth. The inoculated broth cultures will be incubated at 37±2° C. in an incubator shaker operating at 115-125 rpm for 10-12 hours.

Preparation of Negative Control:
   Negative control (vehicle without test material) will be utilized for each tester strain with and without S9 activation.

Preparation of Positive Controls:
   A known mutagen, Dexon (paradimethylaminobenzene diazosulfonic acid sodium salt), will be used as a positive control to demonstrate that tester strains TA98, TA100, and TA1537 are sensitive to mutation to the wild type state. For tester strain TA 1535, sodium azide will be used as a positive control. For tester strain TA100, 2-aminofluorene will be used as a positive control. For tester strain WP2uvrA, 2-aminoanthracene and methylmethane-sulfonate will be used as positive controls. Although metabolic activation is only required with 2-aminofluorene and 2-aminoanthracene to induce mutagenic results, all positive controls will be tested with and without S9 homogenate.

Strain Characteristics and Strain Standard Plate Counts:
   Strain characteristics will be verified and viable counts will be determined.

Spot Plate Inhibition Screen:
   The extract(s) or solubilized material(s) and negative control(s) will be evaluated by a spot plate technique modeled after the antimicrobial zone of inhibition test. This screen is used to evaluate extract or solution concentrations for toxicity which are noninhibitory to the *Salmonella* strains and the *E. coli* strain.

Separate tubes containing 2 ml of molten top agar supplemented with histidine-biotin (for *S. typhimurium*) or with tryptophan (for *E. coli*) will be inoculated with 0.1 ml of culture for each of the five tester strains. After mixing, the agar will be poured across the surface of separate Minimal E plates labeled with lab number, appropriate tester strain, and dose level (when necessary). Once the agar solidifies, sterile filter discs will be placed in the center of the plates. A 0.1 ml aliquot of the extract or solubilized material will be added to the filter discs on each of the labeled plates. Parallel testing will be conducted with a negative control. To demonstrate a positive zone of inhibition, 10× stock Dexon will be used.

The plates will be incubated at 37±2° C. for 2-3 days. Following the incubation period, the zone of growth inhibition will be recorded. If significant inhibition of the background lawn occurs, the extract or solubilized material concentration will be adjusted by preparing one or more dilutions and repeating the inhibition screen to find a nontoxic level.

Standard Plate Incorporation Assay:

Separate tubes containing 2 ml of molten top agar supplemented with histidine-biotin solution (for *S. typhimurium*) or tryptophan (for *E. coli*) will be inoculated with 0.1 ml of culture for each of the five tester strains, and 0.1 ml of the test material. A 0.5 ml aliquot of SWI or S9 homogenate, simulating metabolic activation, will be added when necessary. The mixture will be poured across triplicate Minimal B plates labeled with lab number, appropriate tester strain, and S9 metabolic activation (when applicable). Parallel testing will be conducted on a negative control and five positive controls.

Histidine-free media plates (for *S. typhimurium*) and tryptophan-free media plates (for *E. coli*) will be prepared in triplicate as follows:

1. Extract or solubilized material with and without S9 activation
2. Negative control with and without S9 activation
3. 1× Dexon (known mutagen) with and without S9 activation with strains TA9S, TA100, and TA1 537
4. 1×2-aminofluorene (known mutagen) with and without S9 activation with strain TA 100
5. 1× Sodium azide (known mutagen) with and without S9 activation with strain TA1535
6. 1× 2-aminoanthracene (known mutagen) with and without S9 activation with strain WP2uvrA
7. 1× Methylmethane-sulfonate (known mutagen) with and without S9 activation with strain WP2uvrA The plates will be incubated at 37±2° C. for 2-3 days. After the incubation period, the revertant colonies on each plate (test, negative and positive) will be counted and recorded. The mean number of revertants will be calculated.

Evaluation of Test Results:

The mean number of revertants of the triplicate test plates will be compared to the mean number of revertants of the triplicate negative control plates for each of the five tester strains employed. The means obtained for the positive controls are used as points of reference.

For a test material to be identified as a test failure or "potential mutagen" there must be a 2-fold or greater increase in the number of mean revertants over the means obtained from the negative control, for any/all five tester strains. If no 2-fold increase is present, the test material is considered nonmutagenic.

Any apparent "positive response" will be confirmed by demonstrating a dose-response relationship using three non-toxic dose levels of the test material. There should be a range of concentrations that produce a linear dose response. In the event linearity cannot be established, the assay will be repeated with an appropriate change in dose levels. A test material will be judged mutagenic if it causes a dose-related increase in the number of revertants over a minimum of two increasing dose concentrations.

Test Validity:

For any assay to be considered valid, it must meet the following criteria:

1. Strain characteristics: All *S. typhimurium* tester strains (TA98, TA100, TA1535, and TA1537) must exhibit sensitivity to crystal violet (rfa mutation), and ultraviolet light (uvrB), and must exhibit no growth on biotin plates, and growth on histidine-biotin plates. Tester strains TA98 and TA 100 must exhibit resistance to ampicillin (R-factor); tester strains TA1535 and TA1537 must exhibit sensitivity to ampicillin. Tester strain WP2uvrA must exhibit sensitivity to ultraviolet light, no growth on tryptophan deficient plates, growth on tryptophan supplemented media and sensitivity to ampicillin.
2. Strain Standard Plate Counts: A viable count on the working culture suspensions for each tester strain (TA98, TA100, TA1535, TA1537 and WP2uvrA) should not be less than 1×10 CFU/ml.
3. Spot Plate Inhibition Screen: Each prepared extract or solubilized material will be evaluated for inhibition or toxicity to the cells. A test sample that is noninhibitory to moderately noninhibitory to the tester strains will be tested by the standard plate incorporation method. In the event a test material is inhibitory, dilutions will be required to find a nontoxic level.
4. Standard Plate Incorporation Assay: Each positive control mean must exhibit at least a 3-fold increase over the respective negative control mean of the *Salmonella* tester strain employed, and at least a 2-fold increase over the respective negative control mean of the *E. coli* tester strain. Exceptions include conditions not intended to provoke a mutagenic response (e.g. 2-aminoanthracene and 2-aminofluorene without metabolic activation). The negative control results of each tester strain will exhibit a characteristic number of spontaneous revertants. Spontaneous reversion rates may vary, but should be consistent with the ranges specified (see Table below). The Table is meant as a guideline only. Negative control results for tester strains may fall outside of the range listed. In such an instance, the results should be evaluated with caution.

| Species | Tester Strain | Number of Spontaneous Revertants |
|---|---|---|
| *S. typhimurium* | TA98 | 15-50 |
| | TA100 | 120-240 |
| | TA1537 | 3-28 |
| | TA1535 | 10-35 |
| *E. coli* | WP2uvrA | 20-125 |

References for Example 14

Ames, B. N., McCann, 3, and Yamasaki, E., "Methods for Detecting Carcinogens and Mutagens with the *Salmonella*/ Mammalian-Microsome Mutagenicity Test" Mutation Research 31, (1975): 347-364.

Brusick, D. J., V. F. Simmon, H. S. Rosenlcranz, V. A. Ray, and KS. Stafford, "An Evaluation of the *Escherichia coli* WP2 and WP2uvrA Reverse Mutation Assay," Mutation Research 76, (1980): 169-190.

Maron, Dorothy M., Ames, Bruce N., "Revised Methods for the *Salmonella* Mutagenicity Test," Mutation Research, 113 (1983): 175-215.

ISO 10993-3. Biological Evaluation of Medical Devices, Part 3: Tests for Genotoxicity, Carcinogenicity and Reproductive Toxicity.

OECD Guideline for the Testing of Chemicals, Proposal for Replacement of Guidelines 471 Bacterial Reverse Mutation Test, Document Number 471.

Ortiz, A. J., M. T. Pollastrini, M. Barea, and D. Ordohez, "Bacterial Mutagenic Evaluation of Luxabendazole, a New Broad Spectrum Antihelminic, with the *Salmonella typhimurium* Histidine and the *Escherichia coli* Tryptophan Reversions Tests," *Mutagenesis* 11 (1996): 27-31.

Test validation, Bacterial Mutagenicity Test: NAMSA lab number 98T-00785-00.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A biostable gel prepared by a process comprising:
   (a) curing at least one silicon-containing polyol, polyamine, polyepoxy or polyisocyanate, having 1 or more functional groups and a number average molecular weight of at least 20,000 in the presence of:
   (b) at least one diol, diamine or diisocyanate having a number average molecular weight of less than 10,000; and, optionally,
   (c) an initiator.

2. A biostable gel prepared by a process comprising:
   (a) curing at least one silicon-containing polyol, polyamine, polyepoxide or polyisocyanate having one or more functional groups capable of activation by free radical initiation, and a number average molecular weight of at least 20,000, in the presence of:
   (b) at least one diol, diamine or diisocyanate having a number average molecular weight of less than 10,000; and
   (c) an initiator.

3. A biostable gel according to claim 1 or 2, in which the gel has an average functionality of 1 to 5.

4. A biostable gel according to claim 1, in which the functional groups of component (a) are independently selected from OH, NCO, epoxy and NR'R" in which R' and R" are independently selected from H, $CO_2H$ and $C_{1-6}$ alkyl.

5. A biostable gel according to claim 2, in which the groups capable of activation by free radical initiation contain double or triple bonds.

6. A biostable gel according to claim 5, in which the groups capable of activation by free radical initiation are vinyl or $C_{1-6}$ alkyl acrylates.

7. A biostable gel according to claim 1, the initiator is absent.

8. A biostable gel prepared by a process comprising:
   (a) curing at least one of a silicon-containing polyol, polyamine, polyepoxy, polyvinyl, polyacrylate or polyisocyanate of formula (I) or (II):

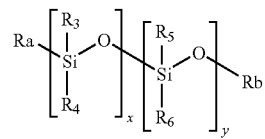

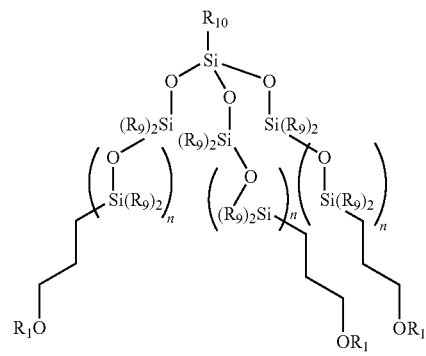

in which $R_a$ and $R_b$ are independently selected from $C_{1-6}$ alkyl, OH, $C_{1-6}$alkoxy, $(CH_2)_3OR_1$ and $Si(R_7)(R_8)(CH_2)_3OR_2$;

$R_1$ and $R_2$ are independently selected from $C_{1-6}$ alkyl optionally substituted with OH, NCO, epoxy or NR'R" in which R' and R" are independently selected from H, $CO_2H$ and $C_{1-6}$ alkyl;

$R_3$ to $R_8$ are independently selected from vinyl, and $C_{1-6}$ alkyl which may be optionally interrupted by O and optionally substituted with OH, NCO, epoxy, $C_{1-6}$alkyl acrylate or NR'R" in which R' and R" are as defined above;

$R_9$ is $C_{1-4}$ alkyl;

$R_{10}$ is optionally substituted $C_{1-4}$ alkyl or

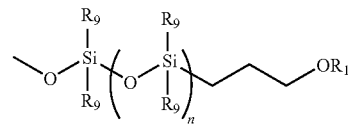

in which $R_1$ and $R_9$ are as defined above;

x is 100 to 1000;

y is 0 to 200; and n is 30 to 500 in the presence of;

(b) at least one diol, diamine or diisocyanate having a weight number molecular weight of less than 10,000; and, optionally (c) an initiator.

9. A biostable gel according to claim 8, in which the silicon-containing polyol, polyamine, polyepoxy, polyvinyl, polyacrylate or polyisocyanate of formula (I) is as follows:

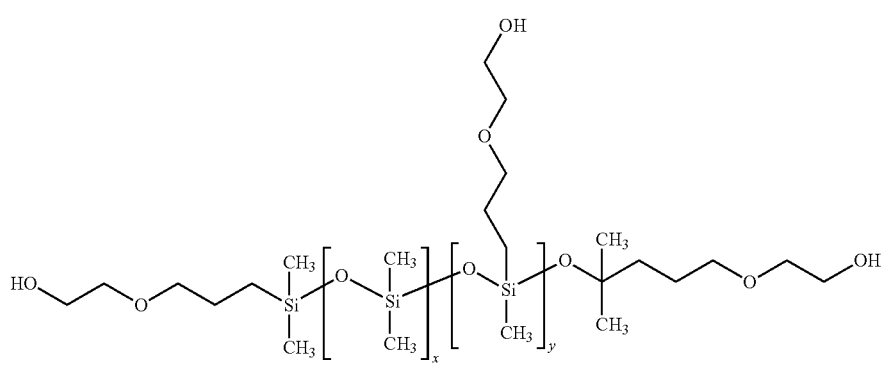
(Ia)
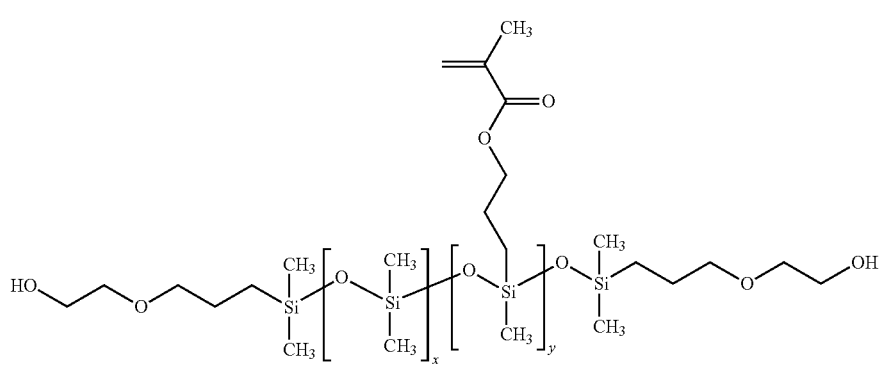
(Ib)
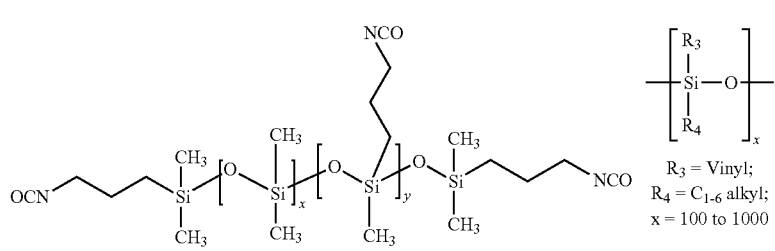
(Id)
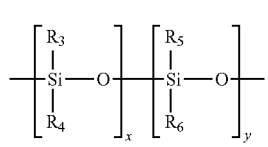
R₃ = Vinyl;
R₄ = C₁₋₆ alkyl;
x = 100 to 1000
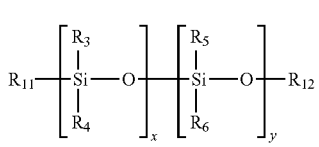
(Ie)
R₃ = Vinyl; R₄, R₅ and R₆ =
C₁₋₆ alkyl; x = 100 to 1000 and
y = 4 to 200
(If)
R₃ = Vinyl;, R₄, R₅ and R₆ =
C₁₋₆ alkyl; R₁₁ and R₁₂ = C₁₋₆ alkyl,
hydroxyl, methoxy and/or ethoxy;
x = 100 to 1000 and y = 4 to 200
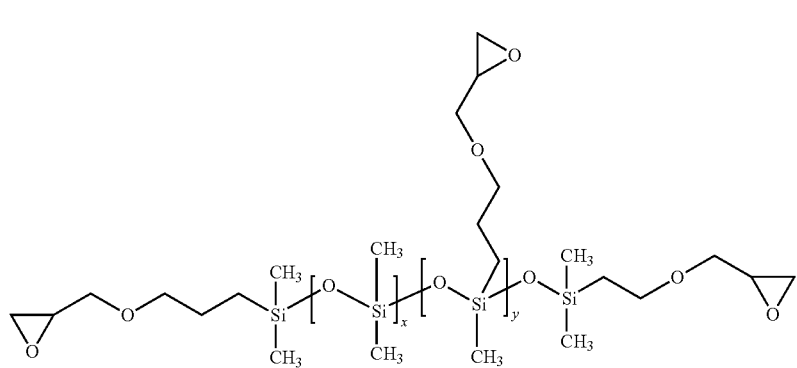
(Ig)

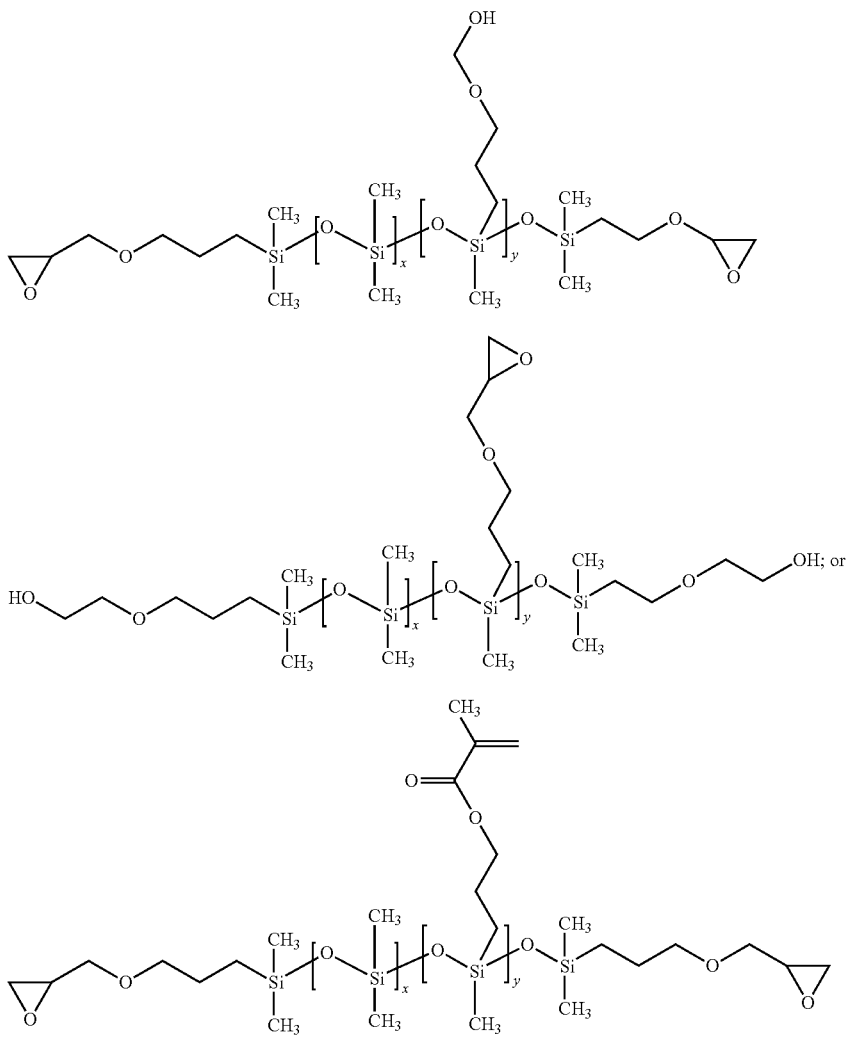

in which x and y in the compounds of formulae (Ia), (Ib), (Ic), (Ig), (Ih) and (Ij) are as defined in claim 8.

10. A biostable gel according to claim 8, in which the silicon-containing polyol, of formula (II) is as follows:

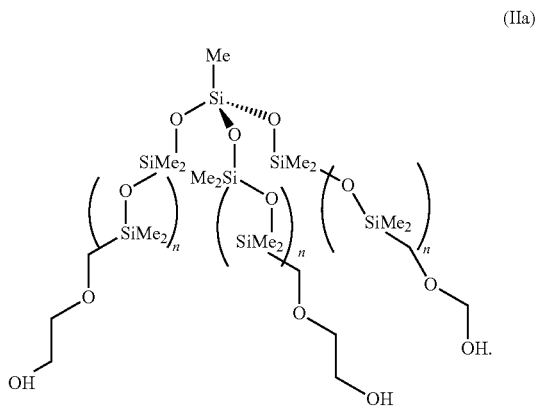

11. A biostable gel according to claim 1, 2, 8, 9 or 10 in which the number average molecular weight of component (a) is 30,000 to 200,000.

12. A biostable gel according to claim 1, 2, 8, 9 or 10 in which the amount of component (a) is 80 to 100% based on the total weight of the gel.

13. A biostable gel according to claim 1, 2, 8, 9 or 10 in which the diol or diamine is a polyether, polycarbonate, polyalkylene or $C_{1-6}$ alkane diol or diamine.

14. A biostable gel according to claim 13, in which the polyether diol or diamine is represented by the formula (III)

$$A\text{-}[(CH_2)_m\text{—}O]_n\text{-}A' \qquad \text{(III)}$$

in which

A and A' are OH or NHR wherein R is H or optionally substituted $C_{1-6}$ alkyl;

m is an integer of 4 or more; and n is an integer of 2 to 50.

15. A biostable gel according to claim 13, in which the $C_{1-6}$ alkane diol is methane diol, butane diol or hexane diol.

16. A biostable gel according to claim 1, 2, 8, 9 or 10 in which the diol or diamine contains silicon.

17. A biostable gel according to claim 16, in which the diol or diamine containing silicon is represented by the formula (V):

$$A-R_{15}-\underset{\underset{R_{13}}{|}}{\overset{\overset{R_{11}}{|}}{Si}}-\left[O-\underset{\underset{R_{14}}{|}}{\overset{\overset{R_{12}}{|}}{Si}}\right]_p-R_{16}-A' \quad (V)$$

in which

A and A' are OH or NHR wherein R is H or optionally substituted $C_{1-6}$ alkyl;

$R_{11}$, $R_{12}$, $R_{13}$ and $R_{14}$ are independently selected from hydrogen or optionally substituted $C_{1-6}$ alkyl;

$R_{15}$ and $R_{16}$ are the same or different and selected from optionally substituted $C_{1-6}$ alkylene, $C_{2-6}$ alkenylene, $C_{2-6}$ alkynylene, arylene or a heterocyclic divalent radical; and p is an integer of 1 or greater.

18. A biostable gel according to claim 17, in which the compound of formula (V) is; 1,3-bis(4-hydroxybutyl)tetramethyl disiloxane (BHTD); or 1-4-bis(3-hydroxypropyl)tetramethyl disiloxane.

19. A biostable gel according to claim 1, 2, 8, 9 or 10 in which the diisocyanate is an aliphatic or aromatic diisocyanate.

20. A biostable gel according to claim 19, in which the aliphatic or aromatic diisocyanate is 4,4'-diphenylmethane diisocyanate (MDI), methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanatonaphthalene (NDI), para-tetramethylxylene-diisocyanate (p-TMXDI), meta-tetramethylxylene diisocyanate (m-TMXDI), 2,4-toluene diisocyanate (2,4-TDI), isophorone diisocyanate (IPDI) or isomers or mixtures thereof.

21. A biostable gel according to claim 20, in which the aromatic diisocyanate is MDI.

22. A biostable gel according to claim 1, 2, 8, 9 or 10 in which the number average molecular weight of component (b) is 500 to 10000.

23. A biostable gel according to claim 1, 8, 9 or 10 in which the initiator is present.

24. A biostable gel according to claim 23, in which the amount of initiator is 0.125% to 5% based on the total weight of the gel.

25. A process for preparing the biostable gel according to claim 1 which comprises the steps of:
mixing components (a) and (b) and optionally (c); and
curing the mixture of (a) and (b).

26. A process for preparing the biostable gel according to claim 25 which comprises the steps of:
(i) preparing a prepolymer having terminally reactive polyisocyanate groups from component (b);
(ii) mixing the prepolymer of step (i) with component (a); and
(iii) curing said mixture.

27. A process according to claim 25 or 26, in which a polyurethane processing additive is added in step (i).

28. A biostable gel which is a reaction product of:
(a) the silicon-containing polyol, polyamine, polyepoxy or polyisocyanate of formula (I) or (II) according to claim 8; and
(b) $C_{1-6}$ alkane diol or diamine, polysiloxane diol or diamine and/or a diisocyanate.

29. A biomaterial, device, article or implant which is wholly or partly composed of the gel according to claim 28.

30. A biomaterial, device, article or implant according to claim 29 which is selected from a soft tissue implant designed to replace and augment tissues; orthopaedic joints or parts thereof; bone suture anchors; reconstructive facial surgery; controlled drug release devices; components in key hole surgery; biosensors; tools and accessories for insertion of medical devices, infusion and flow control devices; and urethral, neurological or vascular bulking agents.

31. A biomaterial, device, article or implant according to claim 30, in which the soft tissue implant is a breast tissue implant and the orthopaedic joint is a spinal disc.

32. A filler material for a medical implant which comprises the gel according to claim 28.

\* \* \* \* \*

UNITED STATES PATENT AND TRADEMARK OFFICE
CERTIFICATE OF CORRECTION

PATENT NO. : 8,623,986 B2
APPLICATION NO. : 12/226508
DATED : January 7, 2014
INVENTOR(S) : Mehrabi et al.

It is certified that error appears in the above-identified patent and that said Letters Patent is hereby corrected as shown below:

On the Title Page

In column 1, under "(73) Assignee", line 1, delete "Aertech" and insert --Aortech--, therefor Item (56)

On page 2, in column 2, under "Other Publications", line 4, delete "1 pgs." and insert --1 pg.--, therefor On page 2, in column 2, under "Other Publications", line 16, delete "1 pgs." and insert --1 pg.--, therefor On page 2, in column 2, under "Other Publications", line 29, delete "India" and insert --Indian--, therefor On page 2, in column 2, under "Other Publications", line 34, delete "Mailed" and insert --mailed--, therefor On page 2, in column 2, under "Other Publications", line 36, delete "3 pg." and insert --3 pgs.--, therefor On page 2, in column 2, under "Other Publications", line 52, delete "Filed" and insert --filed--, therefor On page 2, in column 2, under "Other Publications", line 55, delete "J," and insert --J.,--, therefor Signed and Sealed this
Twenty-fifth Day of November, 2014

Michelle K. Lee
*Deputy Director of the United States Patent and Trademark Office*

CERTIFICATE OF CORRECTION (continued)
U.S. Pat. No. 8,623,986 B2

In the Claims

In column 43, line 49, in Claim 3, delete "get" and insert --gel--, therefor

In column 44, line 45, in Claim 8, delete "alkyl" and insert --alkyl;--, therefor In column 44, line 59, in Claim 8, delete "of;" and insert --of:--, therefor In column 44, line 62, in Claim 8, after "optionally", insert --,--, therefor In column 45-46, equation (Ia), in Claim 9, delete

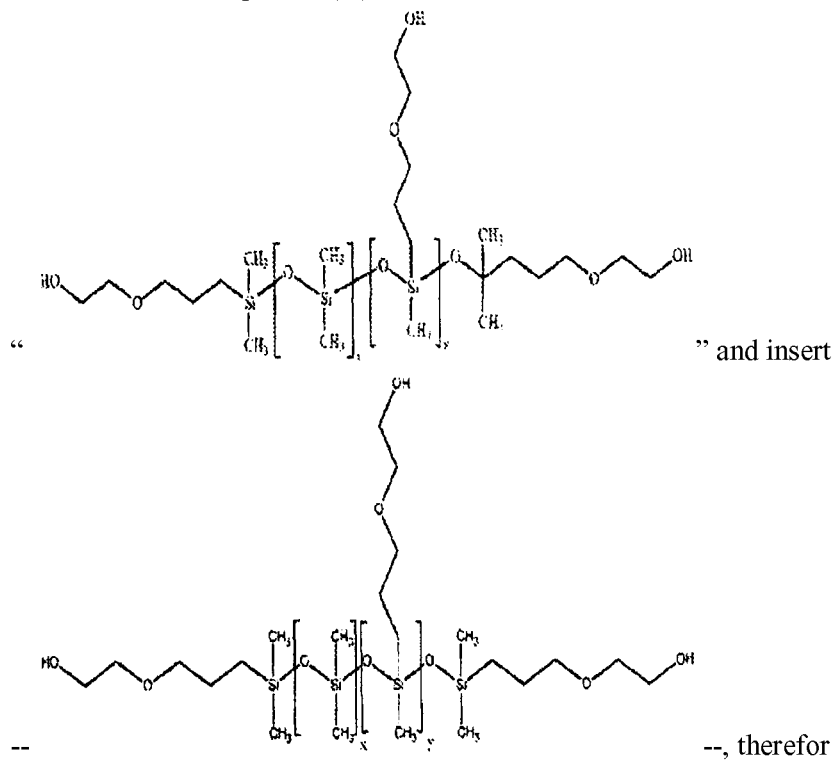

" and insert

--, therefor

In column 46, equation (If) line 1, in Claim 9, delete "Vinyl;," and insert --Vinyl;--, therefor In column 48, line 44, in Claim 11, delete "claim" and insert --claims--, therefor In column 48, line 47, in Claim 12, delete "claim" and insert --claims--, therefor In column 48, line 50, in Claim 13, delete "claim" and insert --claims--, therefor In column 48, line 63, in Claim 16, delete "claim" and insert --claims--, therefor In column 49, line 23, in Claim 19, delete "claim" and insert --claims--, therefor

CERTIFICATE OF CORRECTION (continued)
U.S. Pat. No. 8,623,986 B2

In column 49, line 38, in Claim 22, delete "claim" and insert --claims--, therefor In column 50, line 1, in Claim 23, delete "claim" and insert --claims--, therefor

UNITED STATES PATENT AND TRADEMARK OFFICE
CERTIFICATE OF CORRECTION

| | | |
|---|---|---|
| PATENT NO. | : 8,623,986 B2 | Page 1 of 1 |
| APPLICATION NO. | : 12/226508 | |
| DATED | : January 7, 2014 | |
| INVENTOR(S) | : Mehrabi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1255 days.

Signed and Sealed this
Nineteenth Day of May, 2015

Michelle K. Lee
*Director of the United States Patent and Trademark Office*